(12) United States Patent
Mirotchnik et al.

(10) Patent No.: US 6,630,357 B2
(45) Date of Patent: Oct. 7, 2003

(54) QUANTIFICATION OF BITUMEN USING NMR

(75) Inventors: Konstantin Mirotchnik, Calgary (CA); Kevin Allsopp, Calgary (CA); Apostolos Kantzas, Calgary (CA); Daniel Marentette, Calgary (CA)

(73) Assignee: University Technologies International Inc., Calgary (CA)

( * ) Notice: Subject to any disclaimer, the term of this patent is extended or adjusted under 35 U.S.C. 154(b) by 289 days.

(21) Appl. No.: 09/773,505

(22) Filed: Feb. 2, 2001

(65) Prior Publication Data

US 2002/0081742 A1 Jun. 27, 2002

(30) Foreign Application Priority Data

Nov. 8, 2000 (CA) ............................................. 2325348

(51) Int. Cl.[7] ......................... G01N 24/00; G01N 33/24
(52) U.S. Cl. ........................ 436/173; 436/25; 436/29; 436/31
(58) Field of Search .......................... 436/173, 25, 29, 436/31; 250/255; 324/307, 310, 312, 315

(56) References Cited

U.S. PATENT DOCUMENTS

| | | |
|---|---|---|
| 4,714,881 A | 12/1987 | Givens |
| 5,498,960 A | 3/1996 | Vinegar et al. |
| 5,557,200 A | 9/1996 | Coates |
| 5,696,448 A | 12/1997 | Coates et al. |
| 5,796,252 A | 8/1998 | Kleinberg et al. |
| 5,831,433 A | 11/1998 | Sezginer et al. |
| 5,834,936 A | 11/1998 | Taicher et al. |

OTHER PUBLICATIONS

Podenko et al. "Pulse–modulated nuclear magnetic resonance in rocks enriched in organic matter" Izvestiya Vysshikh Uchebnykh Zavedenii, Geologiya i Razvedka (1988), (4), 115–19.*

A Novel Method for the Estimation of Recoverable Reserves in Oil Reservoirs Using Nuclear Magnetic Resonance (NMR) Relaxometry Paper presented by Mirotchnik, Kantzas, Allsopp, Berman, Aikman and Waymouth—Jun. 8–10, 1998.

Low Field NMR—Tool for Bitumen Sands Characterization: A New Approach, paper by Mirotchnik, Allsopp, Kantzas—Oct. 3–8, 1999.

A new method for Group Analysis of Petroleum Fractions in Unconsolidated Porous Media, paper by Mirotchnik, Kantzas, Starosud and Aikman—Jun. 8–10, 1998.

NMR Properties of Reservoir Fluids, article by Kleinberg and Vinegar in The Log Analyst, Nov.–Dec., 1996.

NMR Relaxation of Clay–Brine Mixtures—article for Society of Petroleum Engineers, by Matteson, Tomanic, Herron, Allen and Kenyon—Sep. 27–30, 1998.

Using NMR Logs to Reconstruct SP and Confirm Rw1—Article by Coates and Miller for The Log Analyst May–Jun., 1998.

* cited by examiner

Primary Examiner—Jill Warden
Assistant Examiner—Yelena Gakh
(74) Attorney, Agent, or Firm—Bennett Jones LLP

(57) ABSTRACT

A method of determining the composition of a sample including heavy oil or bitumen and water using low-field NMR. The NMR spectrum of the sample is taken at relatively low and high temperatures and the oil or water content is determined from the spectra and differential spectrum.

6 Claims, 17 Drawing Sheets

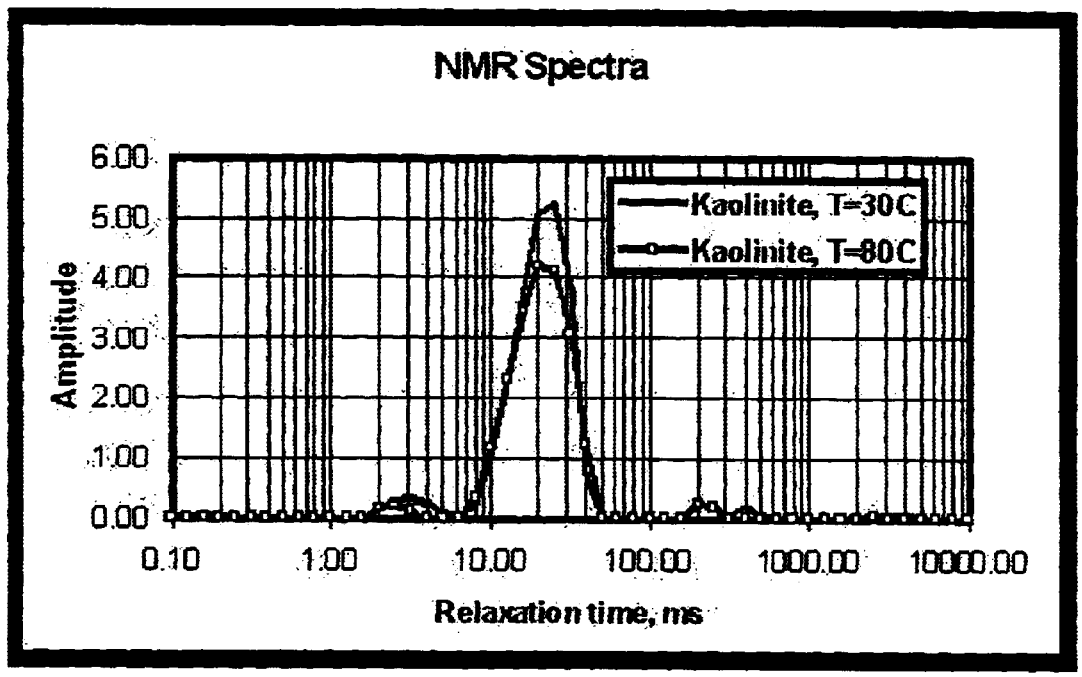
Fig. 1-A
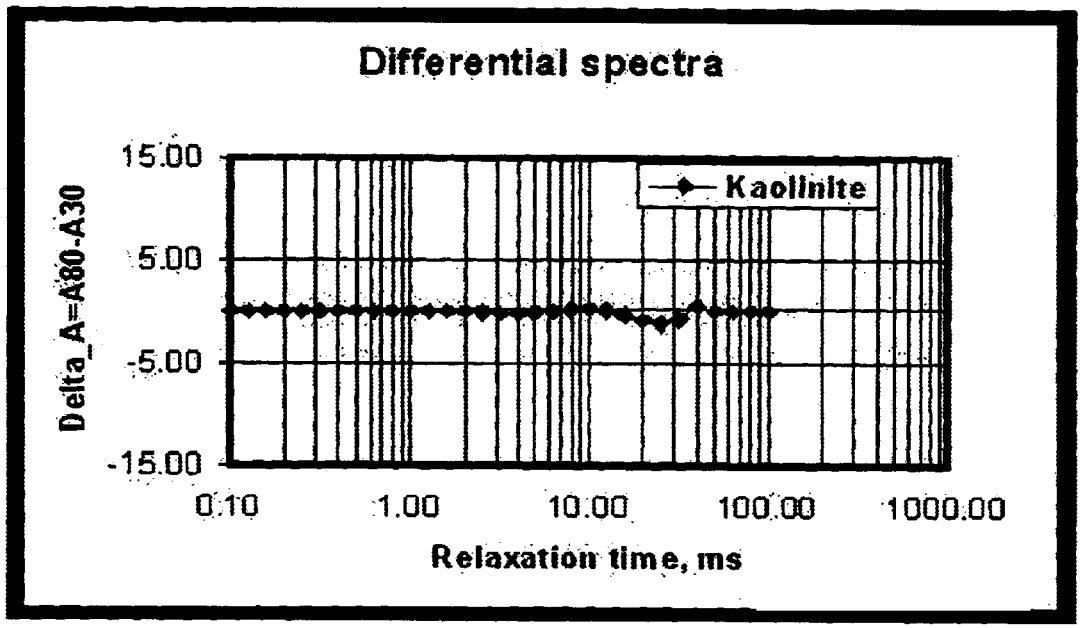
Fig 1-B

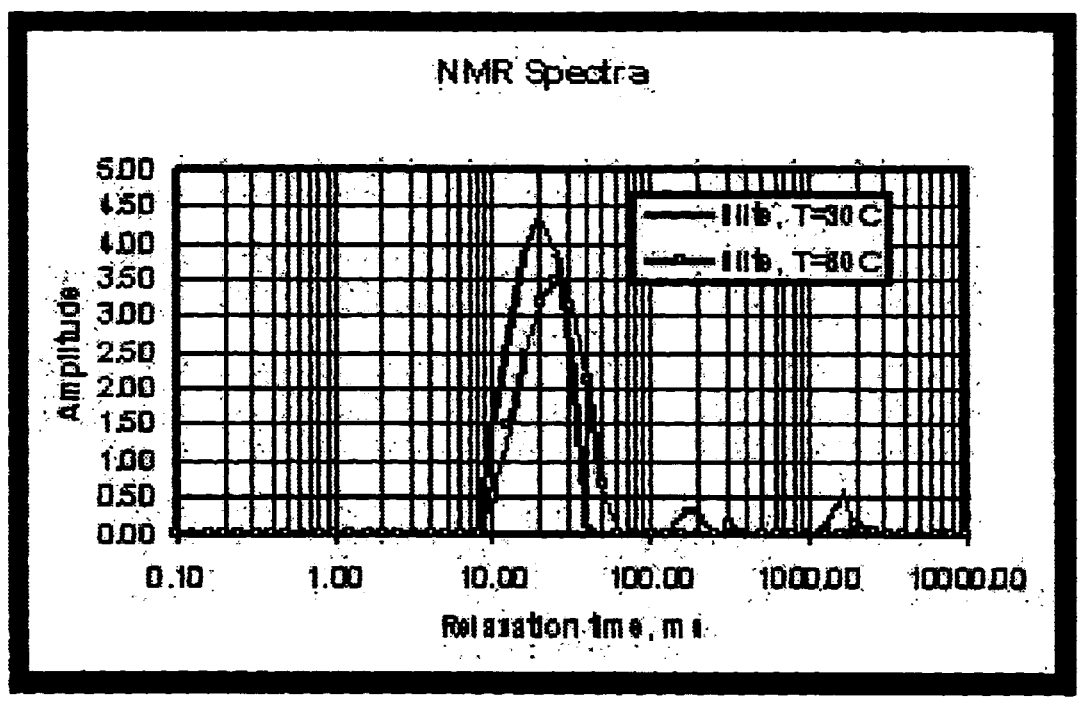
Fig. 2-A
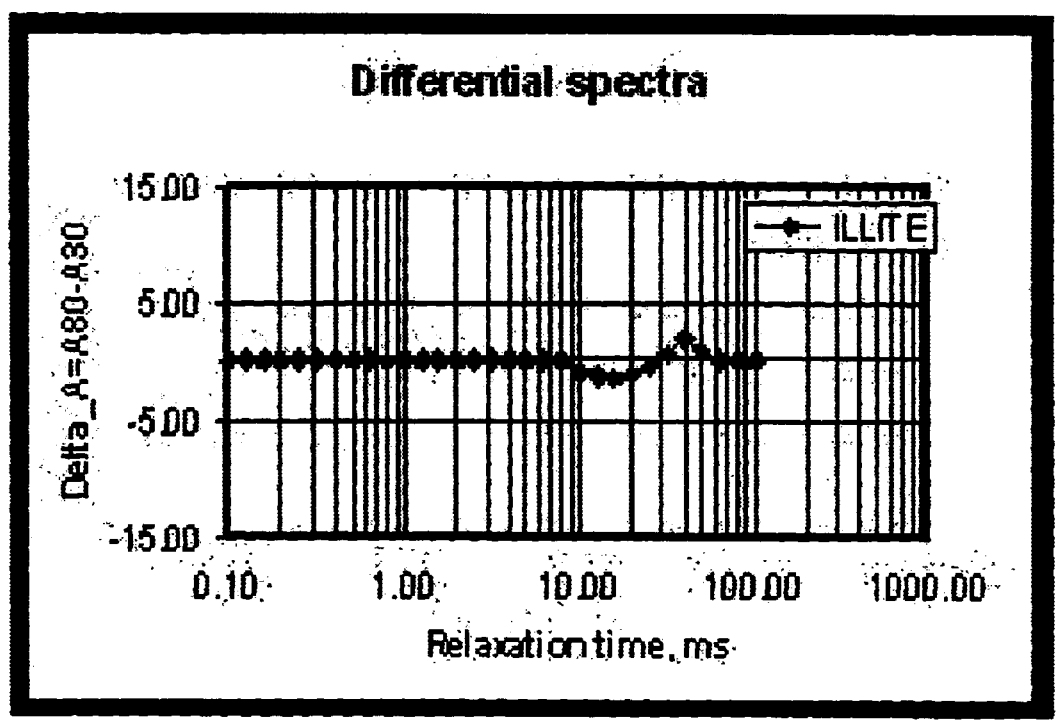
Fig. 2-B

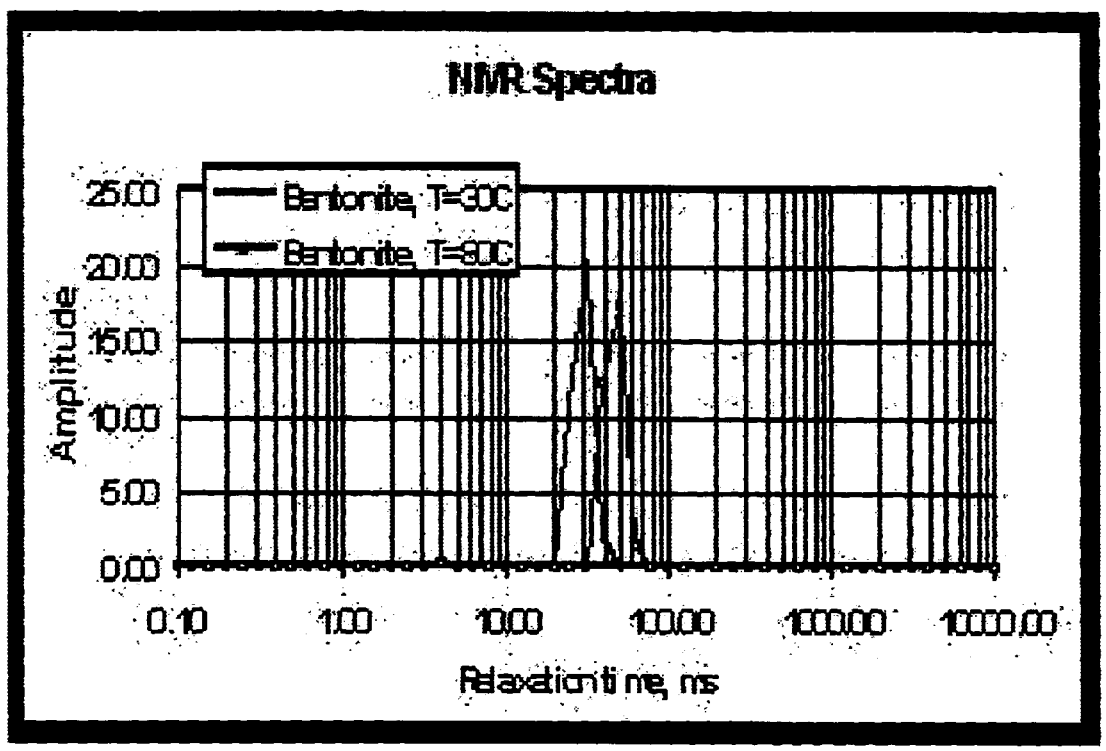
Fig. 3-A
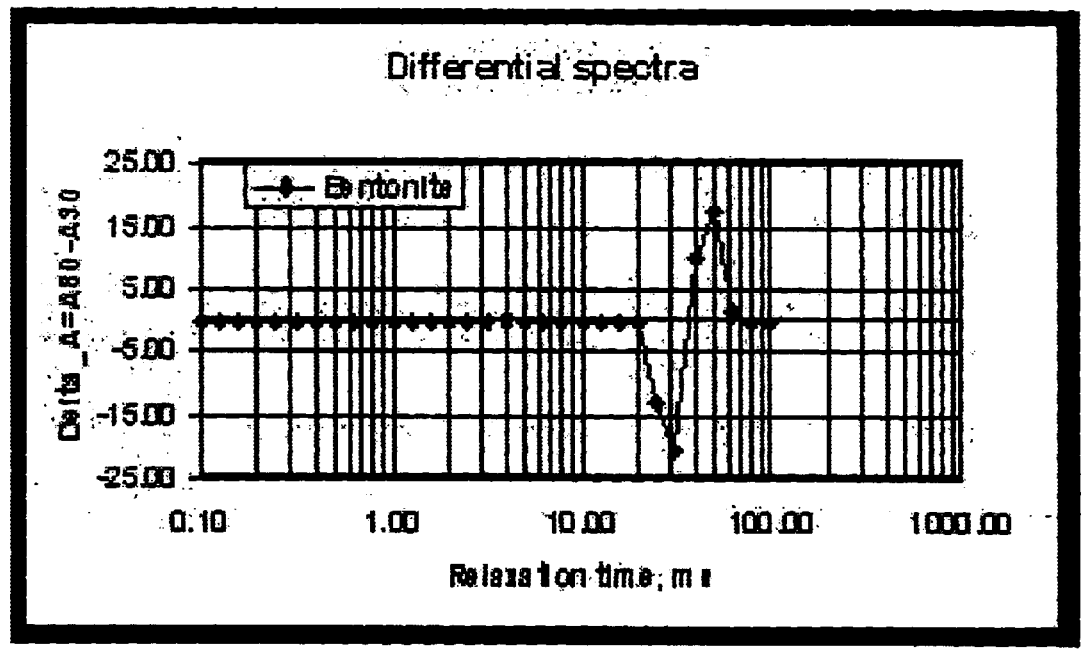
Fig. 3-B

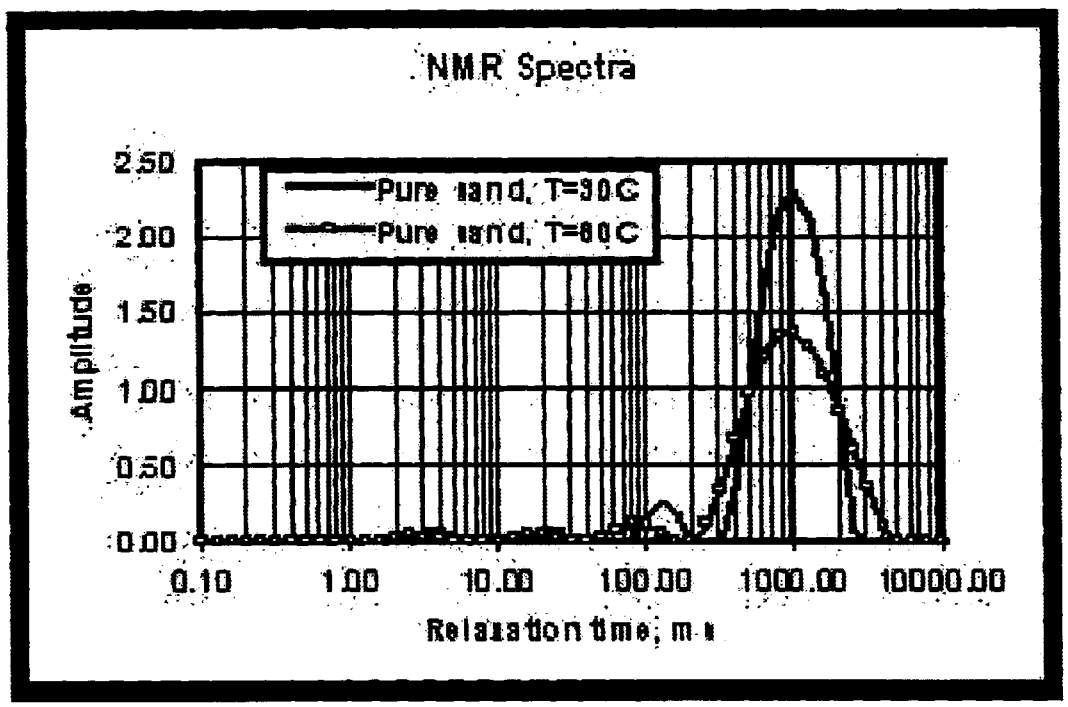
Fig. 4-A
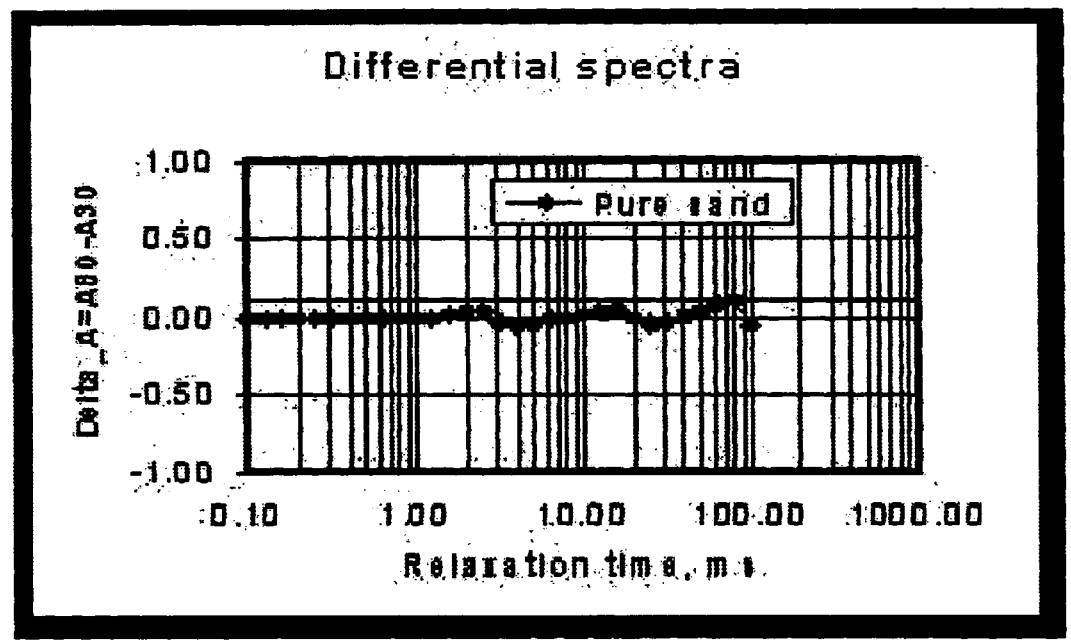
Fig. 4-B

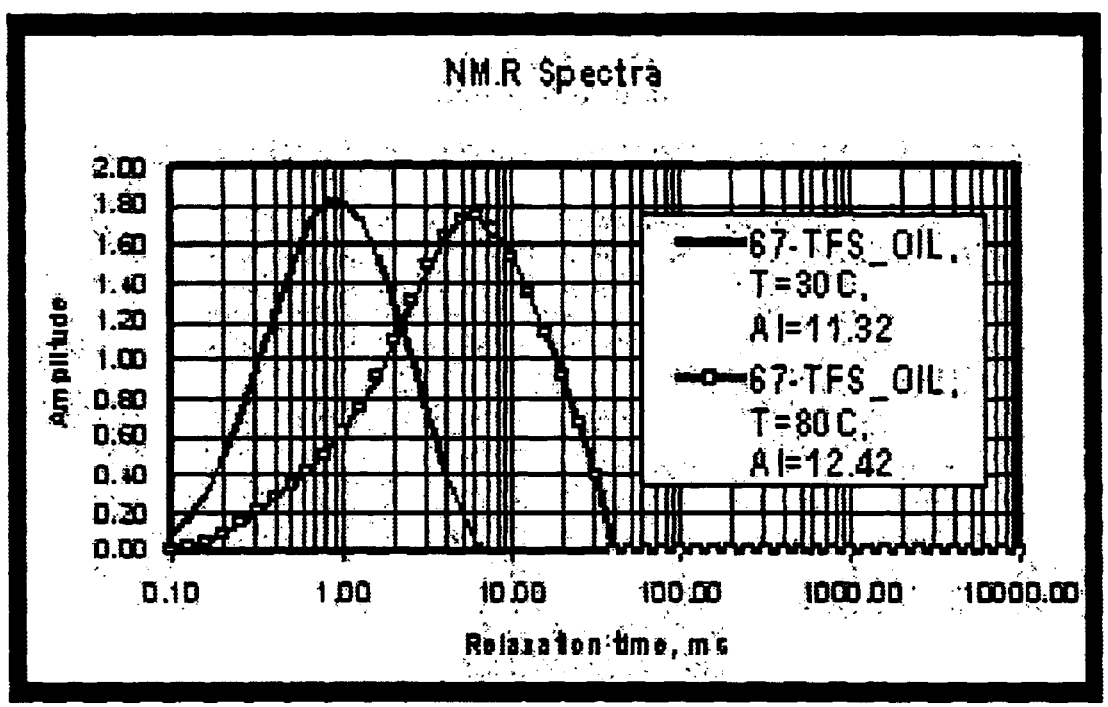
Fig. 7-A
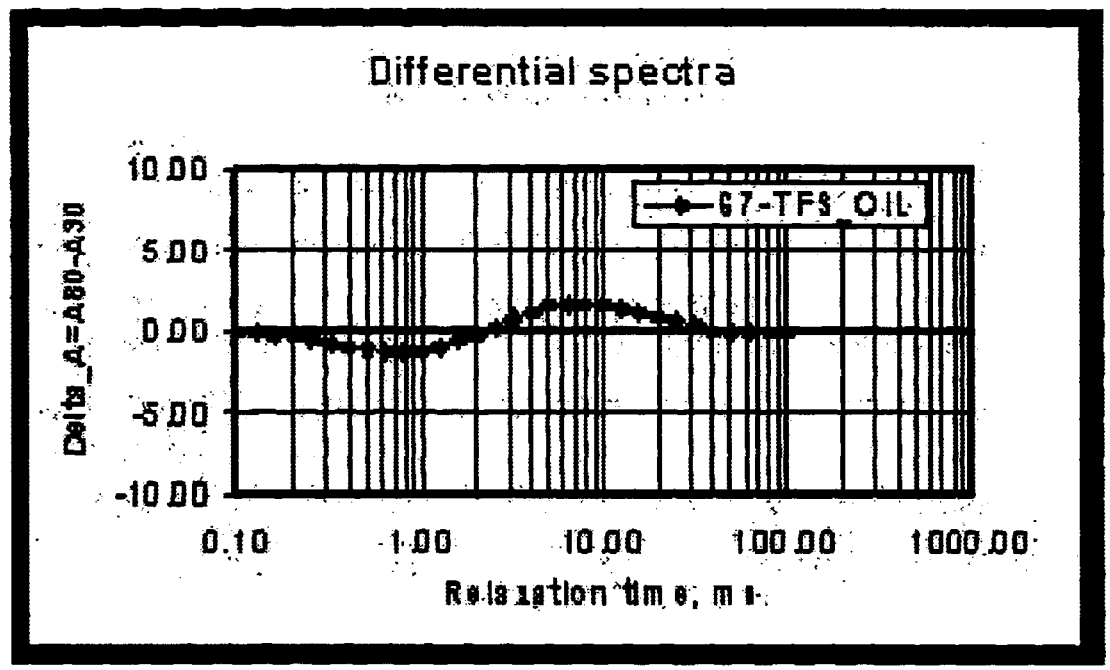
Fig. 7-B

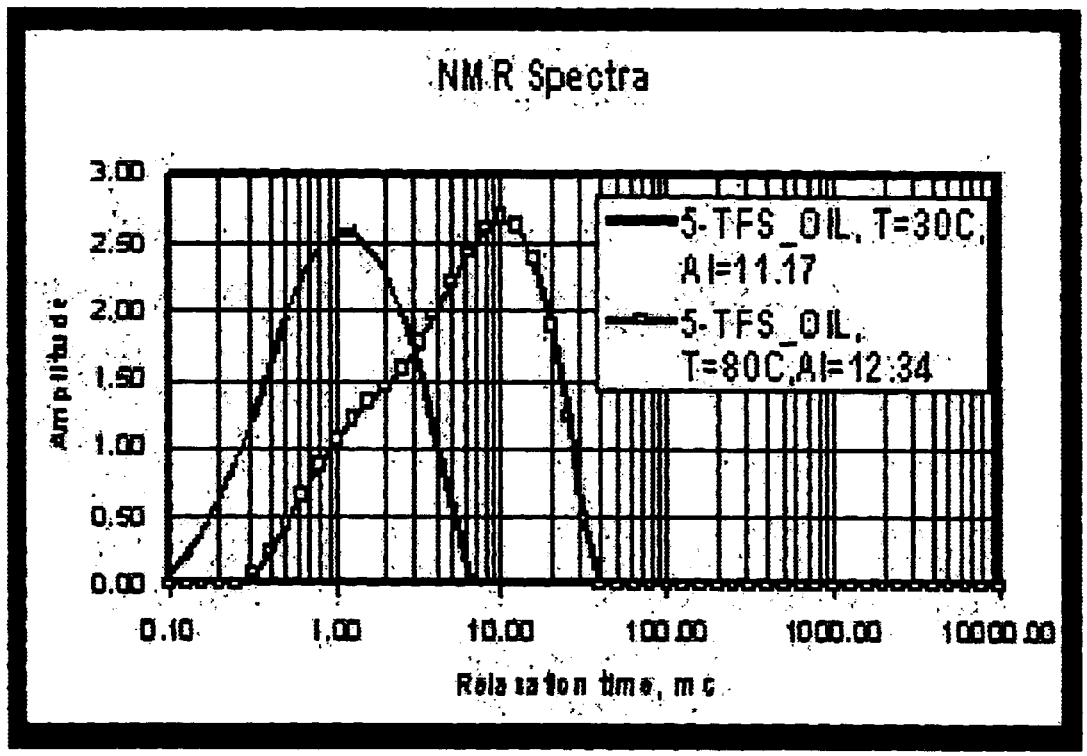
Fig. 8-A
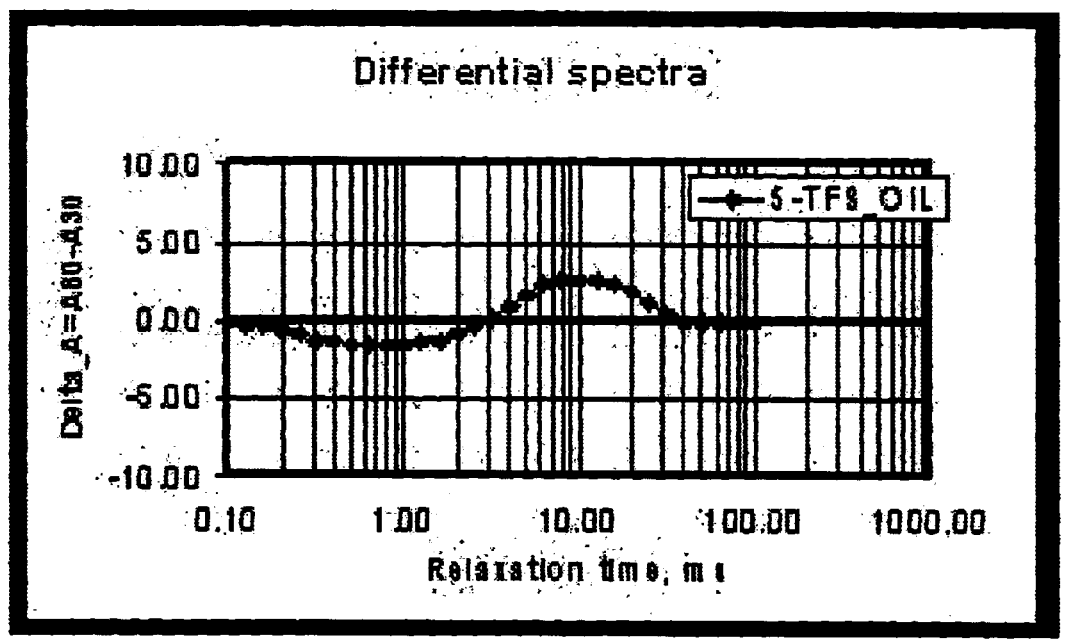
Fig. 8-B

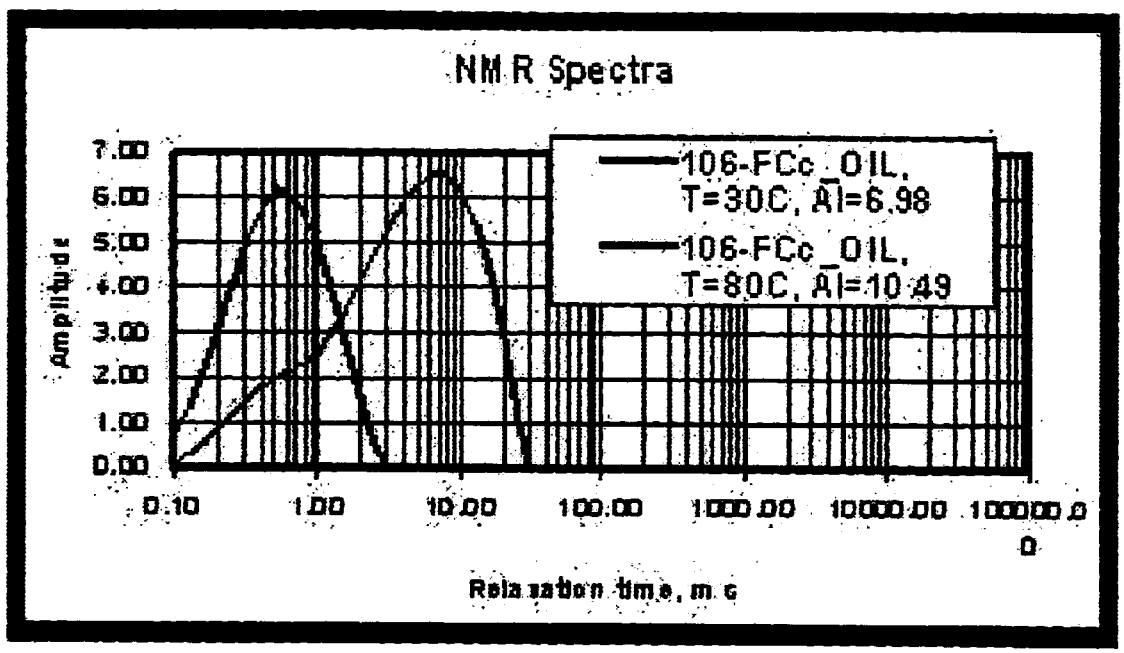
Fig. 9-A
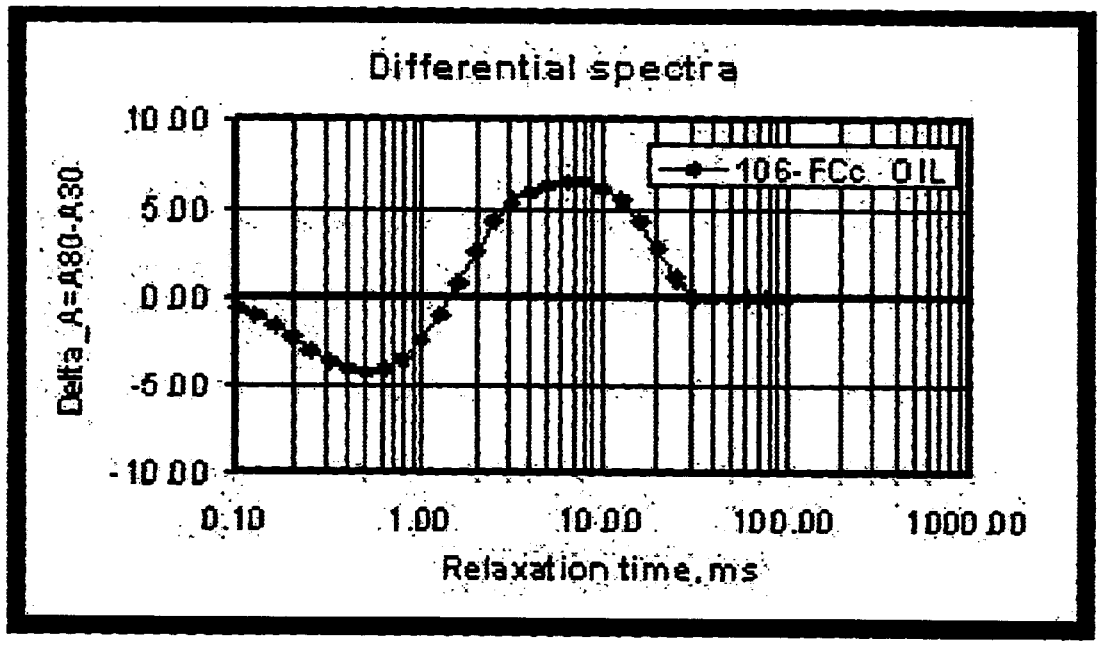
Fig. 9-B

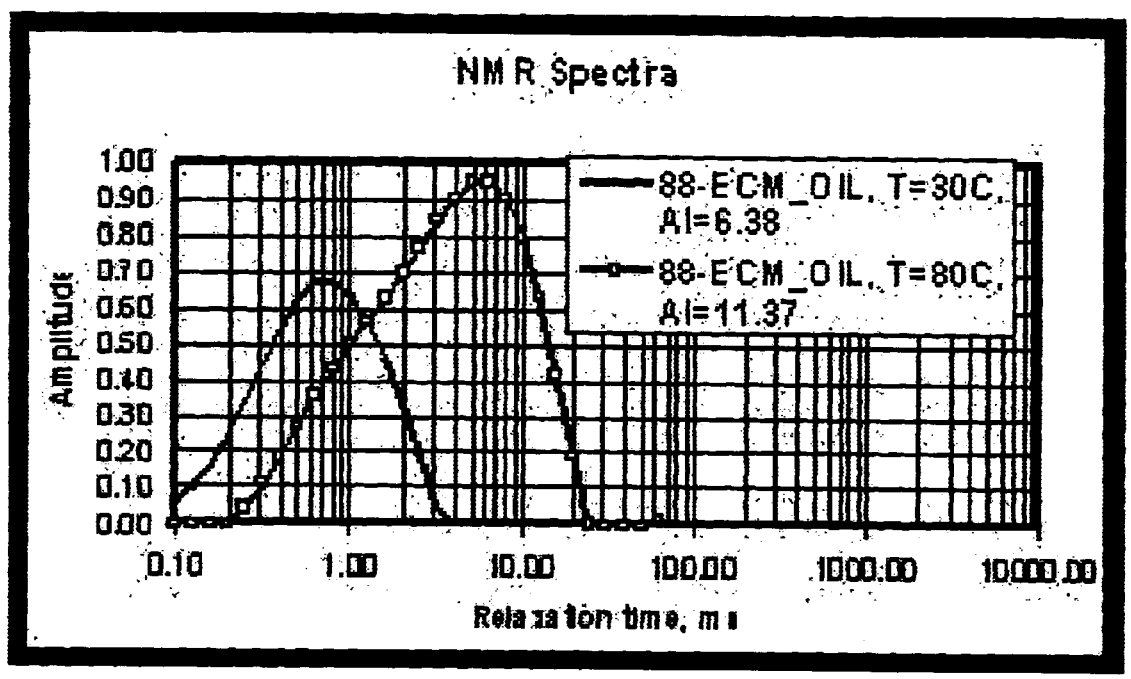
Fig. 10-A
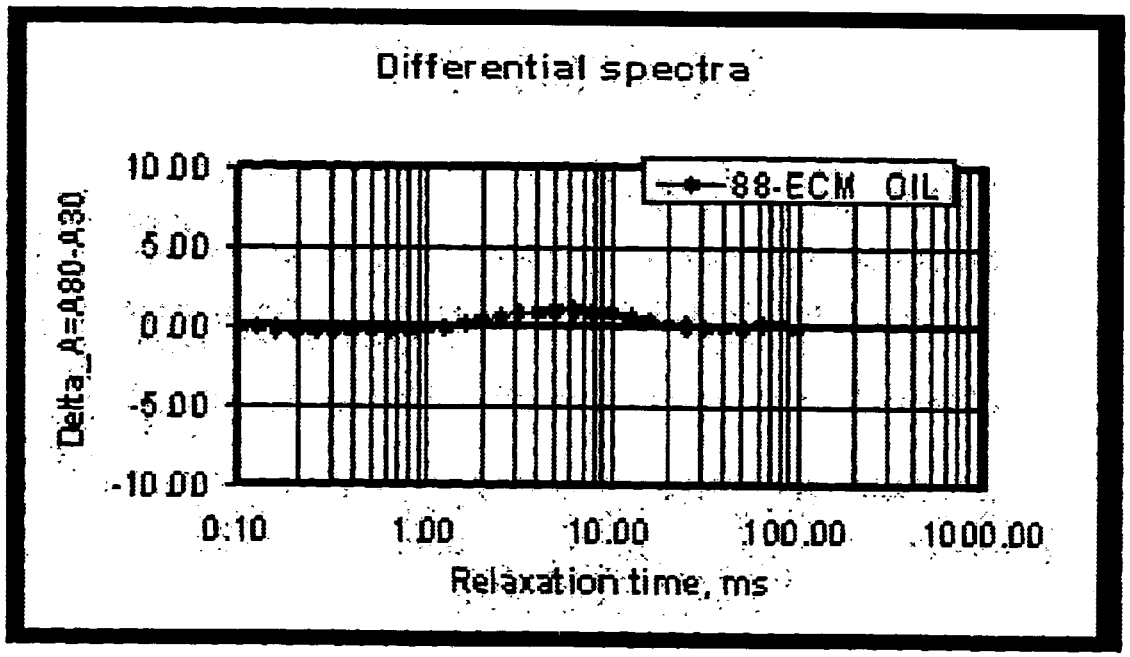
Fig. 10-B

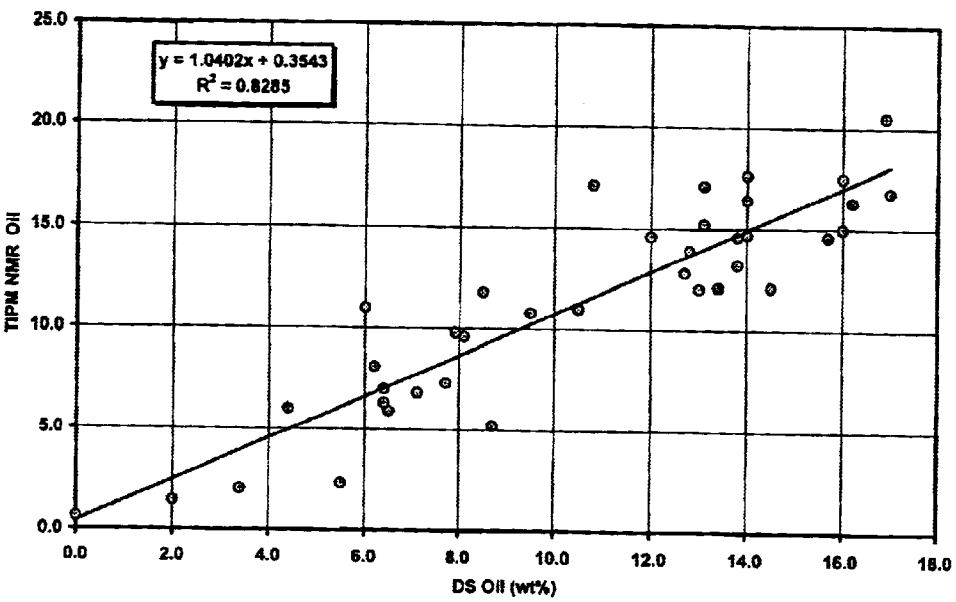
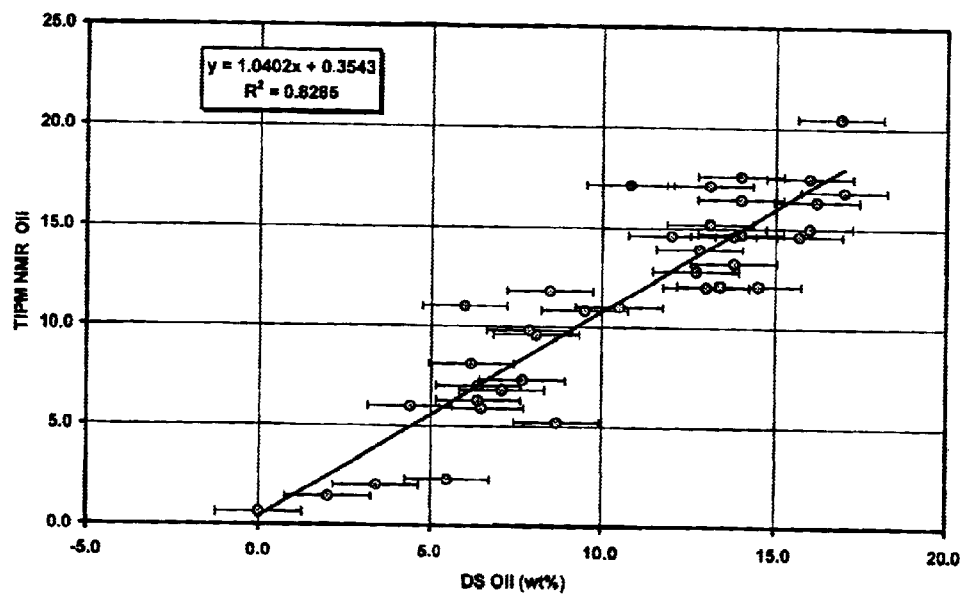

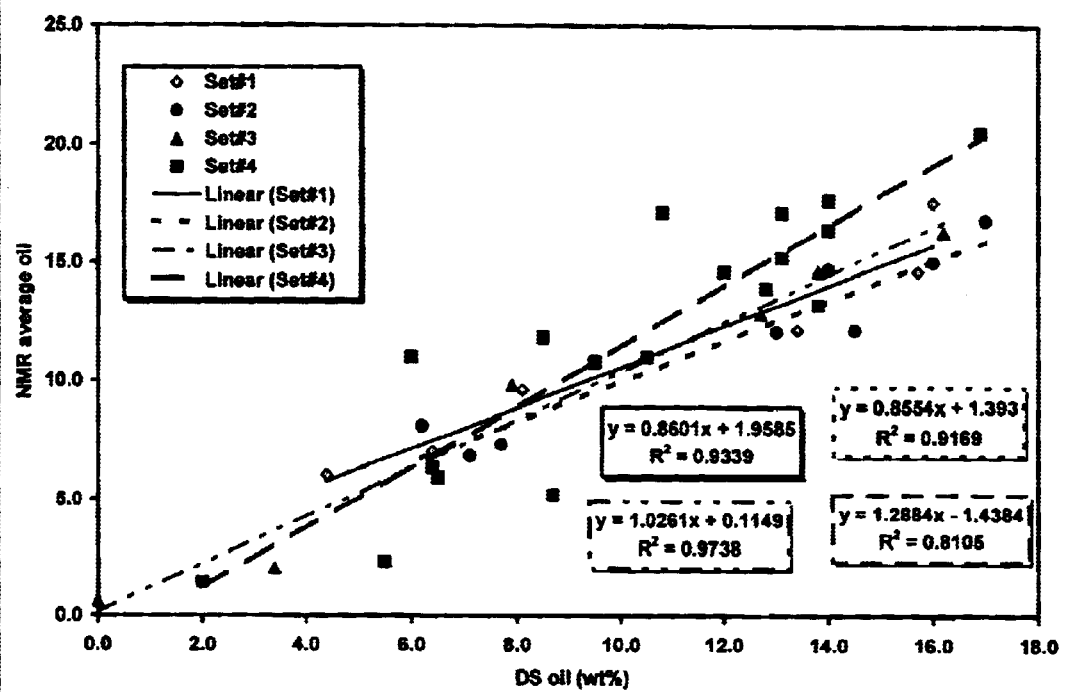
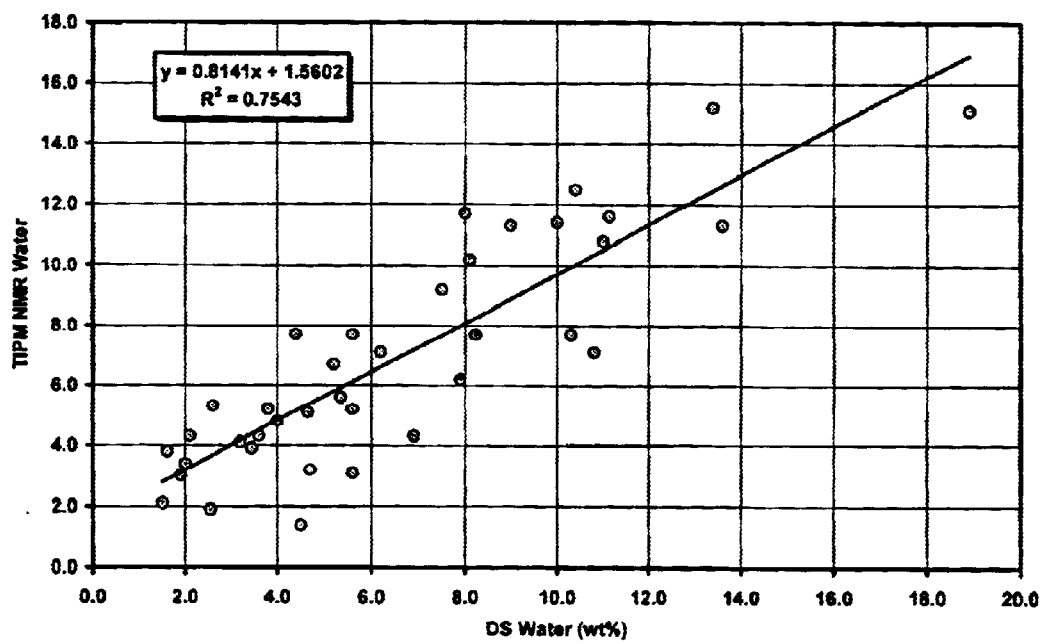

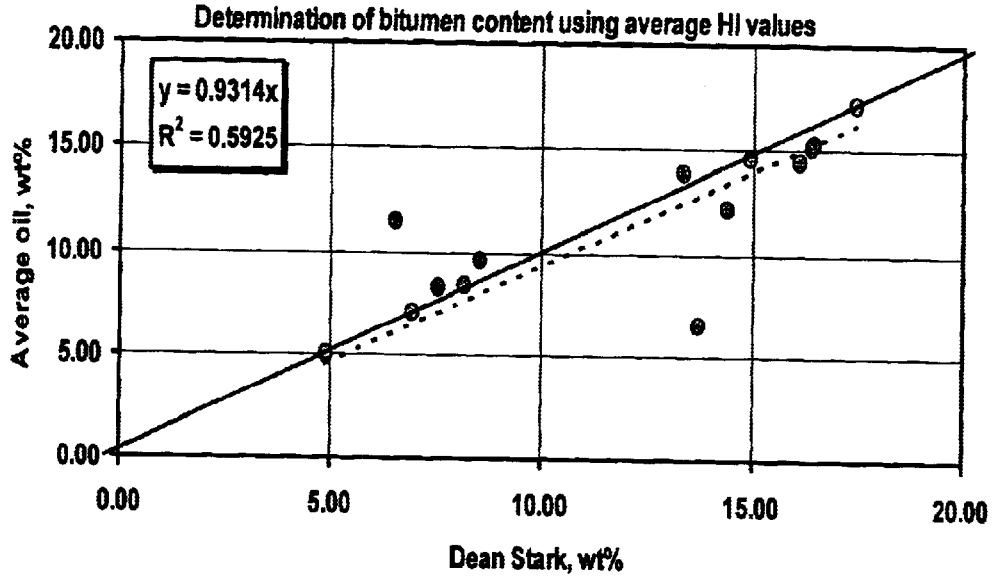
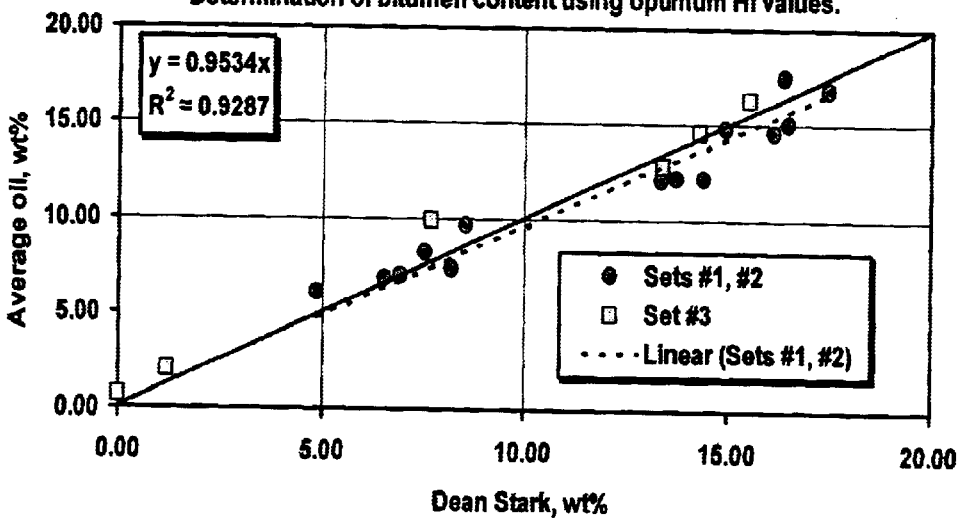

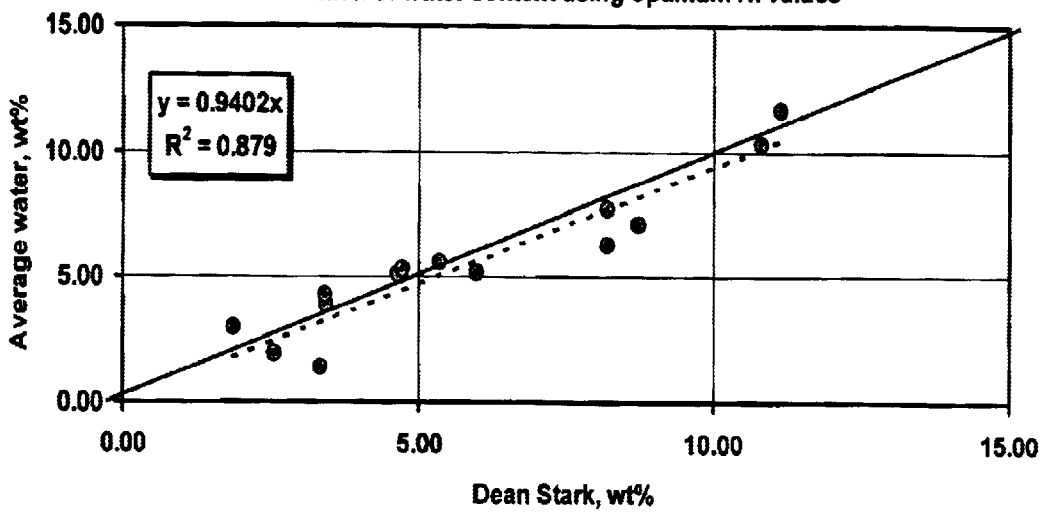
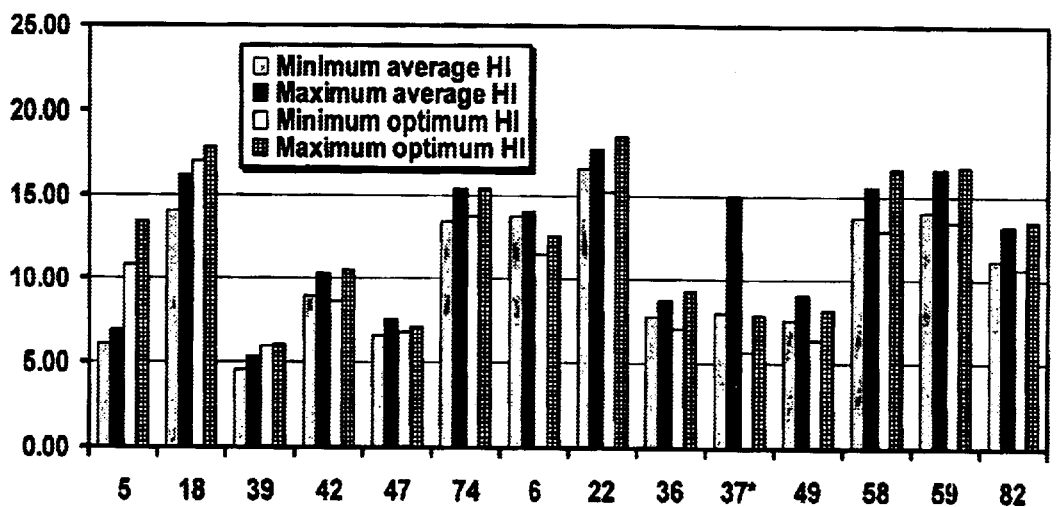

QUANTIFICATION OF BITUMEN USING NMR

FIELD OF THE INVENTION

The present invention relates to nuclear magnetic resonance relaxometry methods for quantifying bitumen and/or water in an ore sample including bitumen, water and solids.

BACKGROUND OF THE INVENTION

Nuclear magnetic resonance ("NMR") relaxometry logging tools are well known in the petroleum and natural gas exploration industry. However, their use has been limited to conventional light oil exploration such as in the Texas chalk formations or the North Sea sandstone formations because conventional low-field NMR does not yield meaningful results when applied to heavy oils and bitumen. The oil typically found in the oil sands deposits found in Northern and Eastern Alberta is heavy oil or bitumen.

The NMR signal obtained from heavy oil and bitumen formations or ore samples can consist of both a hydrocarbon signal and a water signal. Each NMR signal can further characterise both mobile and immobile fluids in porous media. However, as the viscosity of the hydrocarbon phase increases, and the NMR signal shifts towards shorter relaxation times, the composite NMR signal for the sample becomes very complicated. Because of its elevated viscosity, the relaxation characteristics of heavy oil and bitumen become largely undetectable by conventional low-field NMR tools. As a result, conventional methods of NMR detection fail to recognise precisely the hydrocarbon components.

It is useful to determine oil, water and solids content in a sample of bitumen bearing oil sands. Such determination is typically performed with a Dean Stark analysis which is a volumetric technique which relies upon physical separation of the individual components of a sample. However, the accuracy of Dean Stark analysis is sometimes questionable if the analysis is not done in a painstakingly careful manner. If done properly, with a view to accuracy, the analysis is a lengthy and complicated process, requiring specialized equipment.

Therefore, there is a need in the art for a system of determining the oil, water and/or solids content of heavy oil or bitumen bearing oil sands samples utilizing NMR and which provides relatively quick and accurate results.

SUMMARY OF THE INVENTION

The present invention is directed to methods using NMR technology for the quantitative determination of oil, water and solids as an alternative to conventional Dean Stark assays. The present invention is based on the discovery that while the amplitude of the water component of a NMR signal is only weakly temperature dependent, the oil component of the signal is very temperature dependent. At lower temperatures, the bitumen component is largely undetectable by a NMR relaxometer. At an elevated temperature, most of the bitumen component signal may be recovered. The inventors have developed methods by which the amplitude of the bitumen signal may be determined by comparing the low temperature combined signal with the high temperature combined signal. The signal amplitude may then be converted to a weight percentage value.

Therefore, in one embodiment of the invention, the invention is a method of determining the composition of a sample comprising heavy oil or bitumen and water, said method comprising the steps of:

(a) determining the NMR spectrum of the sample at a low temperature between about 0° C. to about 50° C.;
(b) determining the NMR spectrum of the sample at a high temperature between about 50° C. to about 100° C.;
(c) creating a differential spectrum where $\Delta A = A^{High\,T} - A^{Low\,T}$
(d) determining the water content by summing the amplitudes of the low temperature spectrum for the T2 range where 2.5 ms<T2<3000 ms and dividing by the AI of water;
(e) determining the oil content by summing
   i. the amplitudes of the high temperature spectrum in the T2 range where in the differential spectrum, $\Delta A$ has a negative value; and
   ii. the amplitudes of the differential spectrum where $\Delta A$ has a positive value and dividing by the AI of oil at the high temperature.

Preferably, the low temperature is between about 20° C. to about 40° C. and more preferably it is about 30° C. Preferably the high temperature is between about 70° C. to about 90° C. and more preferably it is about 80° C.

The solids content of the sample may be determined by subtracting the oil and water content from the total weight of the sample.

In another aspect, the invention may comprise a system for determining the composition of a sample comprising bitumen or heavy oil and water in a porous media, said system comprising:

(a) means for determining the NMR $T_2$ relaxation time spectrum of the sample at a low temperature between about 0° C. to about 50° C.;
(b) means for determining the NMR $T_2$ relaxation time spectrum of the sample at a high temperature between about 50° C. to about 100° C.;
(c) means for creating a differential spectrum where $\Delta A = A^{High} - A^{Low}$
(d) means for determining the water content by summing the amplitudes of the low temperature spectrum for the $T_2$ range where 2.5 ms<T2<3000 ms and dividing by the AI of water; and
(e) means for determining the heavy oil or bitumen content by summing
   i. the amplitudes of the high temperature spectrum in the T2 range where, in the differential spectrum, $\Delta A$ has a negative value; and
   ii. the amplitudes of the differential spectrum where $\Delta A$ has a positive value; and dividing by the AI of oil at the high temperature.

BRIEF DESCRIPTION OF THE DRAWINGS

The invention will now be described with reference to the attached drawings in which:

FIGS. 1A and 1B are the NMR spectra of pure water and kaolinite at 30° C. and 80° C. and the differential spectrum respectively.

FIGS. 2A and 2B are the NMR spectra of pure water and illite at 30° C. and 80° C. and the differential spectrum respectively.

FIGS. 3A and 3B are the NMR spectra of pure water and bentonite at 30° C. and 80° C. and the differential spectrum respectively.

FIGS. 4A and 4B are the NMR spectra of pure water and pure sand at 30° C. and 80° C. and the differential spectrum respectively.

FIGS. 7A and 7B show the NMR spectrum of a bitumen sample at 30° C. and 80° C. and the differential spectrum respectively.

FIGS. 8A and 8B show the NMR spectrum of a bitumen sample at 30° C. and 80° C. and the differential spectrum respectively.

FIGS. 9A and 9B show the NMR spectrum of a bitumen sample at 30° C. and 80° C. and the differential spectrum respectively.

FIGS. 10A and 10B show the NMR spectrum of a bitumen sample at 30° C. and 80° C. and the differential spectrum respectively.

FIG. 19 shows a graphical comparison of the results obtained from the present invention compared with a prior art analysis.

FIG. 20 shows the results from FIG. 19 with error bar analysis.

FIG. 21 shows the data from FIG. 19 separated into sets 1 through 4.

FIG. 22 shows water analysis results from the present invention compared to the prior art analysis.

FIG. 23 shows a comparison of determination of bitumen content using the present invention compared with the prior art analysis using average HI (AI) values.

FIG. 24 shows the same comparison as FIG. 23 using optimum HI (AI) values.

FIG. 25 shows a comparison of water content determination using the present invention and a prior art analysis using optimum HI (AI) values.

FIG. 26 shows a comparison of minimum and maximum oil predictions using different HI (AI) values.

DETAILED DESCRIPTION OF THE INVENTION

Figure 5:
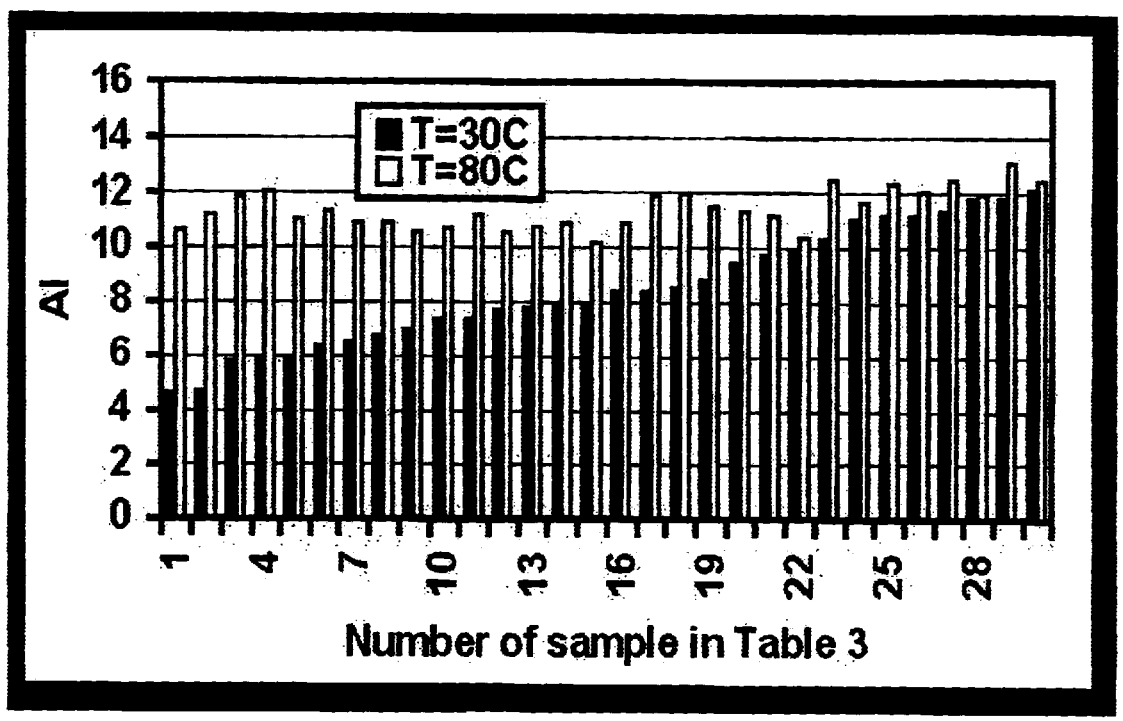
FIG. 5 is a graph showing amplitude index (AI) values for bitumen samples at 30° C. and 80° C.

The present invention provides for methods of characterizing the oil and/or water content of a sample comprising heavy oil or bitumen, water and solids such as sand or clay, whether as a native sample or as a sample taken from a process stream. When describing the present invention, the following terms have the following meanings, unless indicated otherwise. All terms not defined herein have their common art-recognized meanings. The term "oil" shall include "heavy oil" and "bitumen".

A. Definitions

"AI" or "amplitude index" refers to the amplitude of NMR signal for one gram of oil or water at surface temperature and pressure.

"Bitumen" refers to hydrocarbon crude oil normally of viscosity>100,000 cp at room temperature and/or API gravity<10.

"CPMG" refers to the Curr-Purcell-Meiboom-Gill pulse echo method used by NMR tools to measure $T_2$.

"Heavy oil" refers to hydrocarbon crude oil normally of viscosity>20 cp at room temperature and/or API gravity>10 and <20.

"HI" or "hydrogen index" refers to the relative proton density of a sample. The strength or amplitude of a signal is therefore proportional to the the amount of hydrogen in the sample. The HI of pure water at surface temperature and pressure is 1. The HI is proportional to water concentration found in the Concentrative Properties of Aqueous Solutions table for sodium chloride in the CRC Handbook of Chemistry and Physics (1982). As used herein, HI is used interchangeably with AI above.

"NMR" refers to Nuclear Magnetic Resonance which is the technology that uses a magnetic field to influence and measure nuclei spins of certain elements.

"TE" refers to Time Echo [ms]. This is the time-to-echo time. It is defined as the "delay" between pulses.

"$T_2$" refers to the transverse relaxation time measured in milliseconds.

B. Description

The present invention comprises methodologies and apparatuses to determine and quantify components of oil sands during the extraction process. The methodology may be applied to analyze samples from a mine before extraction begins, or from the process stream after mining.

The method of the present invention in one embodiment begins with the step of obtaining the NMR $T_2$ spectrum of the sample, using the CPMG method, at a lower temperature in the range of about 0° C. to about 50° C. The next step is to heat the sample to an elevated temperature in the range of about 50° C. to about 100° C. and to obtain a second NMR spectrum of the sample at the elevated temperature. Preferably, there is a difference of at least about 10° C. between the lower temperature and the elevated temperature and more preferably the difference is at least about 50° C. The low-temperature spectrum and the high-temperature spectrum may then be combined to produce a differential spectrum from which the bitumen fraction and the water fraction of the sample may be determined. The solids fraction may be determined by difference.

The low temperature is preferably between about 20° C. and 40° C. and more preferably about 30° C. The high temperature is preferably between about 70° C. to about 90° C. and more preferably about 80° C.

The system of the present invention comprises a NMR relaxometer, which are well known in the art. A suitable relaxometer is a Corespec-1000™ provided by Numar Corporation operating at about 1 MHz. The methods described herein may be carried by means including general purpose computers programmed with appropriate software, programmable firmware, programmed logic controllers, discrete electronic circuits or any other hardware or combination of hardware and software known to those skilled in the art.

Water Content Determination

NMR measurements for simple fully saturated systems (sand, clay) were performed to understand the frame range for $T_2$ values (min–max) related to the water signal in the ore. Typical experimental results are shown in FIGS. 1 to 4 and in Table 1. FIG. 1a shows the NMR spectra for pure water saturated Kaolinite at both 30° C. and at 80° C. FIG. 1b shows the differential spectrum of the two spectra in FIG. 1a. FIGS. 2a and 2b, 3a and 3b and 4a and 4b are the same for Illite, Bentonite and pure sand respectively.

where $W_w$ is the weight of water (g) and $\Sigma_{i=1}^{n} A_{oi}^{30C}$ is the sum of amplitudes from NMR spectra in $T_2$ frame range 2.5 ms<$T_2$<3000 ms. This parameter is the total amplitude of the NMR signal related to the water content in the porous media. $AI_w$ is the amplitude index for water (amplitude of NMR signal per one g of water).

TABLE 1

NMR parameters for fully saturated simple systems

| Sample ID | Dry Weight [g] | Water Weight [g] | Water Weight by NMR [g] | Ao | T2_ml [ms] | T2_min [ms] | T2_max [ms] | Temp [° C.] |
|---|---|---|---|---|---|---|---|---|
| Kaolinite | 13.00 | 11.09 | 11.39 | 24.1 | 20.1 | 2.0 | 40.0 | 30 |
| Kaolinite | 13.00 | 11.09 | 11.39 | 21.0 | 20.4 | 2.0 | 40.0 | 80 |
| Illite | 12.84 | 9.53 | 9.75 | 20.7 | 23.4 | 10.0 | 40.0 | 30 |
| Illite | 12.84 | 9.53 | 9.75 | 17.7 | 25.2 | 10.0 | 50.0 | 80 |
| Bentonite | 2.04 | 16.55 | 16.85 | 35.5 | 29.4 | 25.0 | 40.0 | 30 |
| Bentonite | 2.04 | 16.55 | 16.85 | 31.2 | 45.7 | 40.0 | 63.0 | 80 |
| Sand | 21.90 | 6.13 | 6.24 | 13.2 | 747.5 | 80.0 | 2500.0 | 30 |
| Sand | 21.90 | 6.13 | 6.24 | 11.0 | 753.5 | 63.0 | >3900 | 80 |

The NMR amplitude value at 80° C. is reduced according to the Curie effect. This effect is clearly shown when the differential spectra are plotted (FIGS. 1b, 2b, 3b, and 4b). The differential spectra are created by subtracting the $T_2$ spectra recovered at 30° C. from the spectra recovered at 80° C. Representative $T_2$ values are presented in Table 1. An estimation of the benefits of using differential spectra for water content measurements can be made using the following transformation:

$$DA\% = [(A_{oi}^{80C} - A_{oi}^{30C}) / A_{oi}^{30C}] * 100$$

where DA is the differential amplitude, $A_{oi}^{80C}$ is the amplitude of the NMR signal for the ith-bin in the 80° C. spectra and $A_{oi}^{30C}$ is the same parameter for the ith-bin in the 30° C. spectra.

The experimental results show that for all simple water saturated systems the following correlation exists at 30° C.:

$$|DA| < 2\% @ T_2 < 10 \text{ ms}$$

The following conclusions can be drawn from the data presented in FIGS. 1 to 4 and Table 1:

The amplitude of the NMR signal at 80° C. is smaller than the amplitude of the NMR signal at 30° C. (Curie effect).

Shift in the $T_2$ spectra during sample heating was observed only for water saturated bentonite.

DA NMR signals from water in porous media recovered at different temperatures can not be more than 2% at $T_2$<20 ms at 30° C. and 80° C.

Therefore, the NMR signal at 30° C. is used to determine the water content in the ore. The water content in ore samples can be determined from the NMR spectra using the following equation:

$$W_w = \sum_{i=1}^{n} A_{oi}^{30C} / AI_w$$

Bitumen Content Determination

In order to determine the NMR signal of the bitumen in the ore, the NMR signal of the bulk bitumen must be investigated first. This investigation is necessary for the identification of the proper splitting parameters in the NMR signal of bitumen-water saturated systems.

Figure 6:
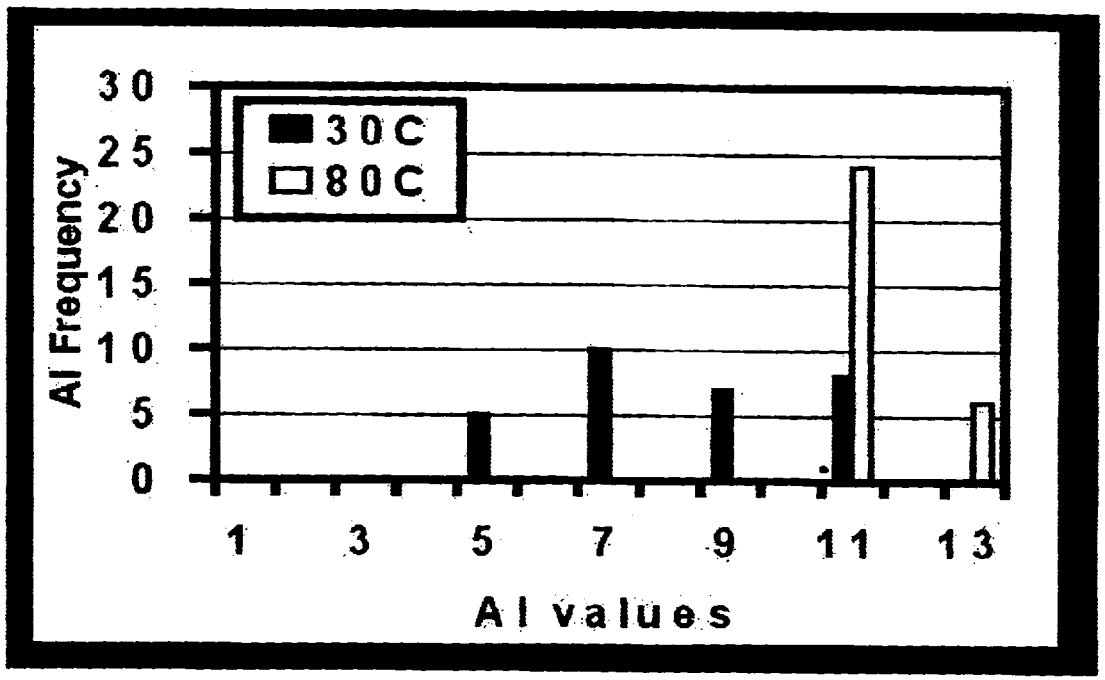
FIG. 6 shows AI value frequency of bitumen samples at 30° C. and 80° C.
Figure 11:
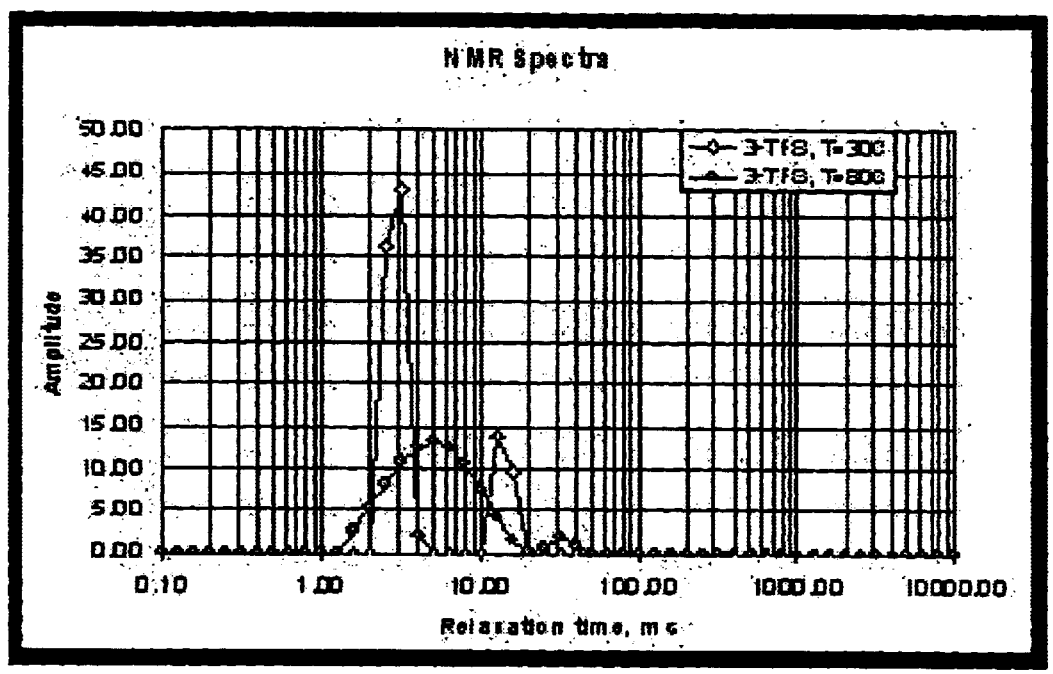
FIG. 11 shows the NMR spectra of a bitumen ore sample at 30° C. and 80° C.
Figure 12:
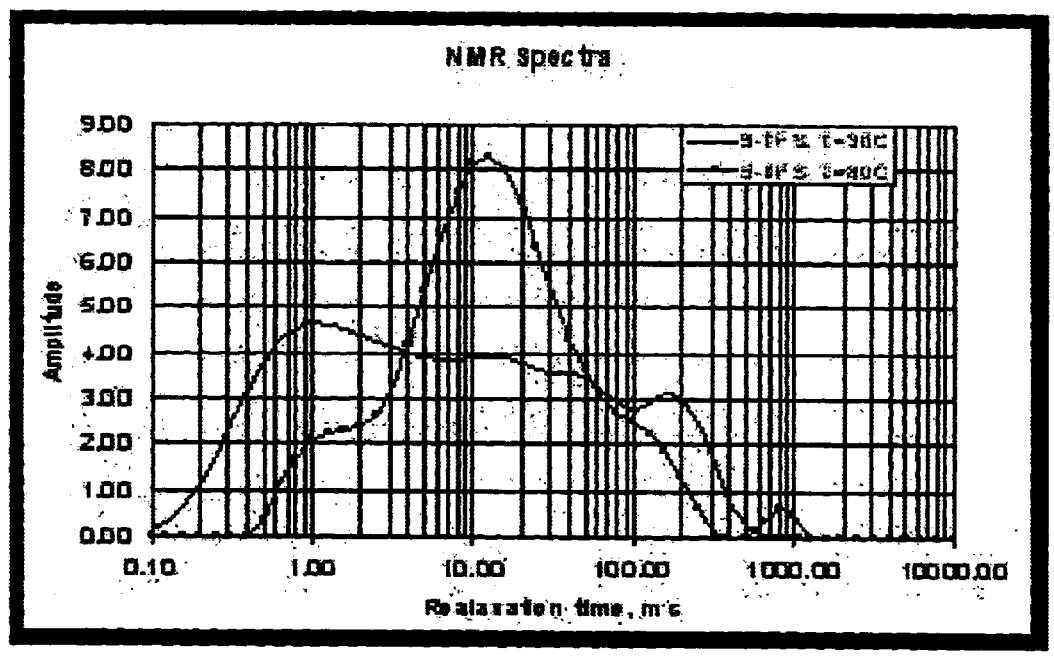
FIG. 12 shows the NMR spectra of a bitumen ore sample at 30° C. and 80° C.
Figure 13:
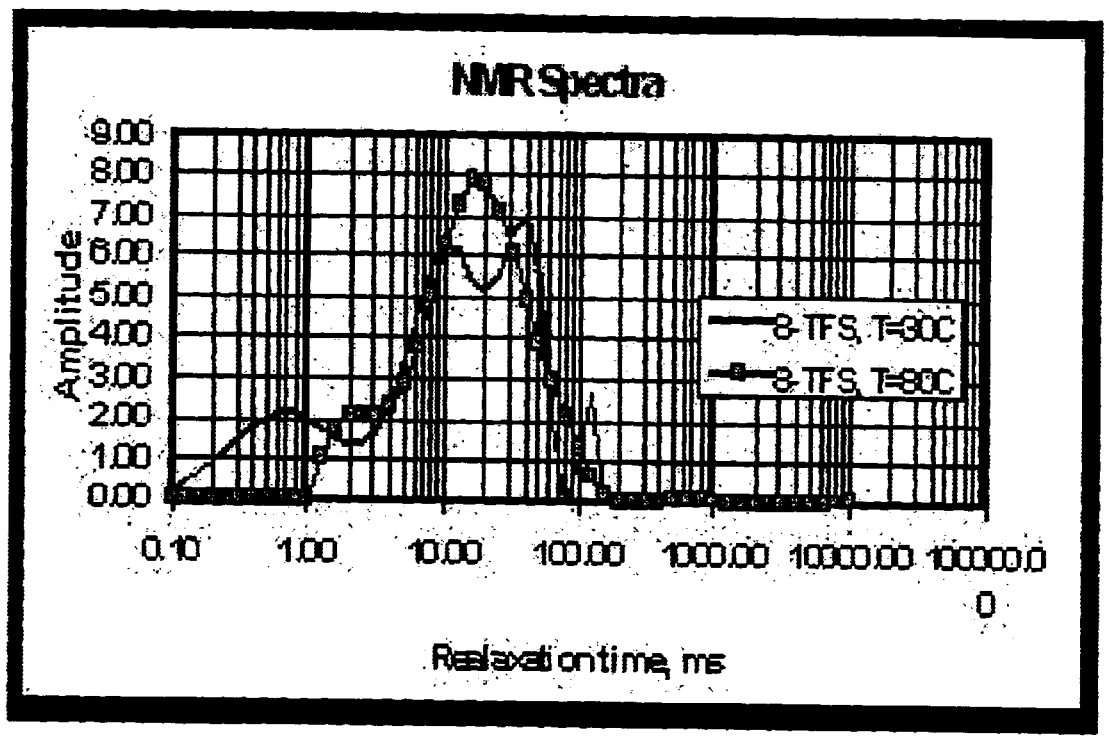
FIG. 13 shows the NMR spectra of a bitumen ore sample at 30° C. and 80° C.
Figure 14:
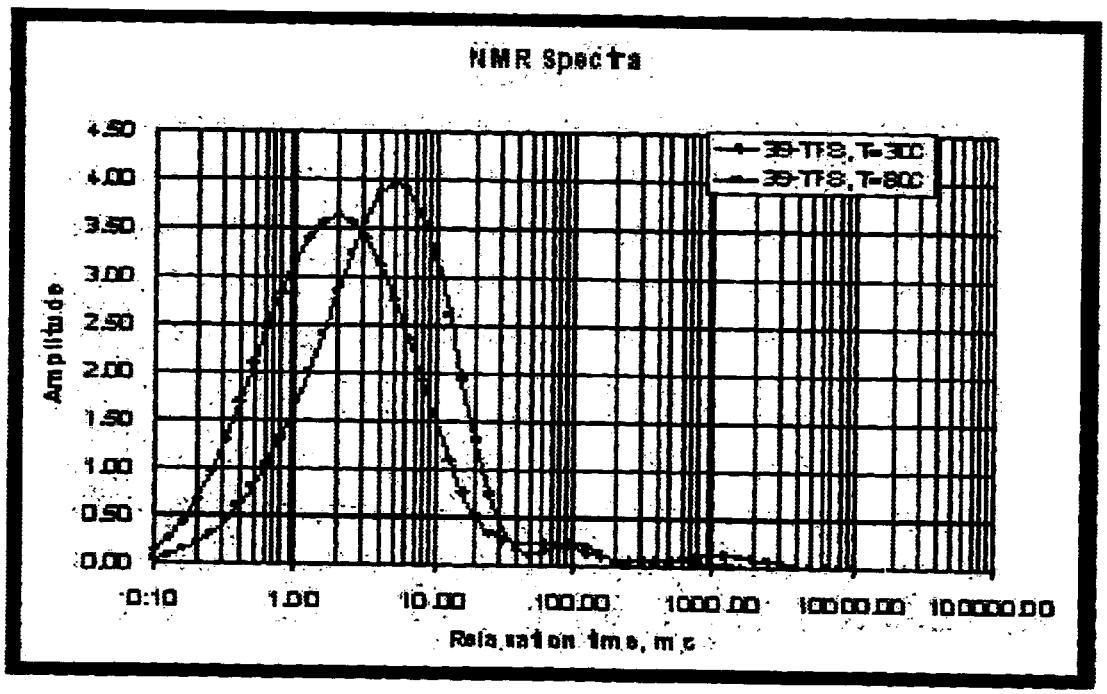
FIG. 14 shows the NMR spectra of a bitumen ore sample at 30° C. and 80° C.
Figure 15:
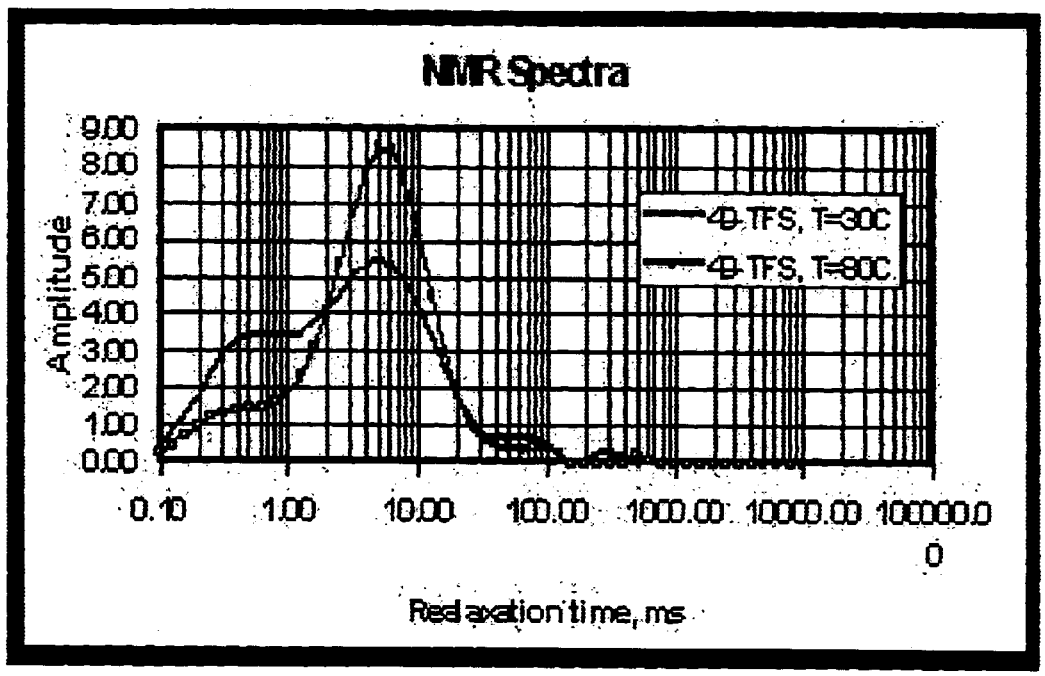
FIG. 15 shows the NMR spectra of a bitumen ore sample at 30° C. and 80° C.
Figure 16:
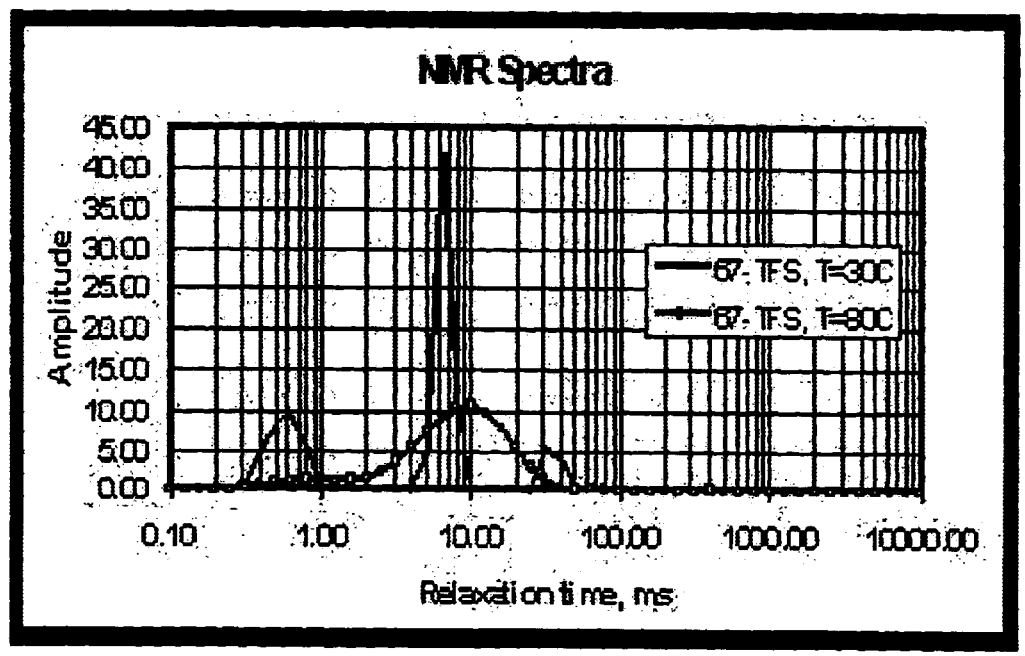
FIG. 16 shows the NMR spectra of a bitumen ore sample at 30° C. and 80° C.

Centrifuge recovered bulk bitumen samples were measured at 30° C. and 80° C. respectively. The amplitude index $(AI_b)$ was calculated for each oil sample at the two different temperatures. Experimental data is presented in Table 2 and FIG. 5. The histogram for $AI_b$ frequency at different temperatures (FIG. 6) shows that the $AI_b$ values are more stable at 80° C. This fact is related to the ability to measure the full NMR signal from the bitumen samples at 80° C. when the viscosity of the sample is decreased and the bitumen molecules are more mobile.

The NMR spectra and the results of the data processing for four displaced bitumen samples are presented in Table 3 and FIGS. 7a and 7b, 8a and 8b, 9a and 9b and 10a and 10b.

The $T_2$ frames corresponding to bitumen NMR spectra at 30° C. temperature do not interfere with the frames that correspond to the NMR spectra for water saturated systems. This simple observation allows us to divide the NMR signal from water and bitumen in the ore samples at this temperature. It is known that the transverse relaxation times $(T_2)$ for liquids are shorter when the liquids are present in porous media in comparison to the $T_2$ values for the same liquids in bulk state. This observation is an additional tool for improving the procedure for splitting the water and bitumen NMR signal at 30° C.

TABLE 2

AI for bulk (recovered) bitumen

| ID_PIC | HI_30 | HI_80 | ID_SAM |
|---|---|---|---|
| 3 | 4.53 | 10.6 | 110(set4) |
| 2 | 4.65 | 11.19 | 59 |
| 3 | 5.75 | 11.83 | 5 |
| 4 | 5.79 | 12.01 | 47 |
| 5 | 5.84 | 11.00 | 82 |
| 6 | 6.38 | 11.34 | 88(set4) |
| 7 | 6.48 | 10.89 | 154(set4) |

TABLE 2-continued

AI for bulk (recovered) bitumen

| ID_PIC | HI_30 | HI_80 | ID_SAM |
|---|---|---|---|
| 8 | 6.75 | 10.93 | 127(set4) |
| 9 | 6.98 | 10.49 | 106 |
| 10 | 7.27 | 10.64 | 65 |
| 11 | 7.27 | 11.21 | 145(set4) |
| 12 | 7.69 | 10.54 | 58 |
| 13 | 7.75 | 10.76 | 42 |
| 14 | 7.85 | 10.88 | 18 |
| 15 | 7.87 | 15.90 | 74 |
| 16 | 8.37 | 10.88 | 22 |
| 17 | 8.38 | 11.84 | 58(set4) |
| 18 | 8.52 | 11.95 | 51 |
| 19 | 8.79 | 11.49 | 77(set4) |
| 20 | 9.41 | 11.29 | 82(set4) |
| 21 | 9.65 | 11.19 | 118(set4) |
| 22 | 9.88 | 10.36 | 6 |
| 23 | 10.29 | 12.46 | 36 |
| 24 | 11.02 | 11.61 | 64(set4) |
| 25 | 11.17 | 12.34 | 5(set4) |
| 26 | 11.18 | 12.01 | 16(set4) |
| 27 | 11.32 | 12.42 | 67(set4) |
| 28 | 11.77 | 11.92 | 57(set4) |
| 29 | 11.78 | 13.14 | 22(set4) |
| 30 | 12.07 | 12.47 | 49 |

TABLE 3

NMR parameters for four displaced bitumen samples

| Sample ID | T2_ml [ms] | T2_min [ms] | T2_max [ms] | Temperature [° C.] |
|---|---|---|---|---|
| B1 | 0.9 | 0.1 | 2.5 | 30 |
| B1 | 5.2 | 0.3 | 20.0 | 80 |
| B2 | 1.2 | 0.1 | 5.0 | 30 |
| B2 | 8.1 | 0.3 | 32.0 | 80 |
| B3 | 1.4 | 0.1 | 5.0 | 30 |
| B3 | 5.0 | 0.3 | 32.0 | 80 |
| B4 | 0.7 | 0.1 | 2.5 | 30 |
| B4 | 6.0 | 0.1 | 25.0 | 80 |

The bitumen content in the ore can be determined according to following procedure. First, the total NMR amplitude in the frame range of $T_2 \leq 2.5$ ms from the low temperature (30° C.) spectrum is determined. The bitumen content is calculated in the ore samples using the amplitude index for bitumen ($AI_b$). The $AI_b$ value is calculated from the 30° C. spectra of bulk bitumen, which is measured from a centrifuge-recovered bulk bitumen sample. Calculations have to be done with the $T_2$ spectra that corresponds to the measurements with TE=0.3 ms. This number is the minimal estimation of the bitumen in the porous media.

The total NMR amplitude related to bitumen from the differential spectra in the frame of $0.1 \text{ ms} < T_2 \leq 25$ ms is then determined. The total amplitude is calculated according to following procedure:

$$A_0^b = \sum_{i=1}^{n} A_{oi}^{80C} + \sum_{j=i+1}^{m} A_{oj}^{diff}$$

where $\Sigma_{i=1}^{n} A_{oi}^{80C}$ is the sum of the amplitudes from the high temperature (80° C.) NMR spectrum for the ore sample corresponding to the $T_2$ frame range related to the area with negative values of amplitude on the differential spectra. $\Sigma A_{oj}^{diff}$ is the sum of the amplitudes from the differential NMR spectrum. Only the positive differential amplitudes have to be involved in the calculation. These amplitude values are related to the NMR signal from bitumen during the heating process. The $A_o^b$ values are determined only for the two cycles presented on the differential spectra related to the nature of the differential NMR spectra from bitumen in the bulk volume. As shown in FIGS. 7B, 8B, 9B and 10B, bitumen can be characterised just by two cycles in the differential spectrum. One is negative and another is positive. The bitumen content may then be determined as follows:

$$W_b = A_0^b / AI_b^{80C}$$

where $W_b$ is the bitumen content in the ore and $AI_b^{80C}$ is the amplitude index for bitumen at 80° C. temperature.

After the oil and water content of a sample is determined, the solids content may be determined by difference:

$$W_s = W_s - W_l$$

where $W_s$ is the total sample weight and $W_l$ is the total weight of bitumen and water.

C. EXAMPLES

The following examples are illustrative but not limiting of the invention disclosed herein.

Example 1

In the first example, samples of ore from Shell Canada's Muskeg River bitumen mine were provided by Shell. The methodology for the determination of water/bitumen/and solids content for all the ore samples that were received from Shell followed the procedure described below. Analysis was also undertaken using conventional Dean Stark analysis in two separate laboratories, to compare with and confirm the results of the present invention.

Four sets of ore samples were received. These samples were marked "AS IS" and they were kept in the freezer. The weight of all "AS IS" samples was recorded.

Each sample was then split in two approximately equal parts.

One part was packed in small vials with weight measurements before (weight of bottle, weight of sample and combined weight) and total weight after packing and taping the sample.

The second part of each sample was weighed and stored for use in bitumen extraction through a centrifugal process.

The centrifugal process was performed in two ways depending on the type of the ore samples. For samples that were visually estimated as bitumen rich samples the centrifugal process includes the following steps: a heavy NaCl brine solution (15% wt) was prepared. The centrifuge rotor cups (inclined position set) were filled with no more than 200 g of sample per cup. The cups that contained ore sample were then filled with brine and were balanced. The centrifuge rotor and cups were heated to 40° C. in an oven. Subsequently the cups were loaded into the rotor and the rotor was placed in the centrifuge. Bitumen displacement was carried out at 40° C. and 15,000 RPM for two hours. For samples that were visually estimated as poor bitumen saturated ore, with or without a large amount of clay, the centrifugal process includes the following steps: a heavy NaCl brine solution (15% wt) was prepared. The centrifuge rotor cups (horizontally positioned) were filled with no more than 60 g of sample per cup. Bitumen was displaced from the samples by the standard forced imbibition procedure. Spinning was performed in two steps. The first step was at 40° C. and 6,000 RPM for 12 hours. The second step was at 60° C. and 4,000 RPM for 4 hours. Bitumen and the remaining ore were collected in the same procedure as described above. When bitumen was displaced from the ore it was collected and it was placed in vials. The sample was weighed before (weight of bottle, weight of sample and combined weight) and after taping.

The ore that remained in the cups after spinning was also collected and stored. The ore also contained some bitumen that for the purposes of this work will be called "irreducible" bitumen.

All NMR measurements were performed using a Numar Corespec 1000™ relaxometer. $T_2$ measurements were made using the CPMG techniques which are well known in the art. The NMR magnet set-up was at 30° C. The relaxometer was tuned twice per day and tuning was done using a sealed standard sample (permanent amount of doped water with $T_2$~240 ms) and a standard tuning procedure. All NMR measurements were performed at two temperatures: 30° C. and 80° C. The magnet was set up at the same temperatures.

A measurement in the NMR at 30° C. consists of the following steps

Time Echo: TE=0.3 and 0.6 ms (twice per TE)

Delay time: TR≦15.0 sec

Number of echoes: NE=25

A measurement in the NMR at 80° C. consists of the following steps

Time Echo: TE=0.3 and 0.6 ms (twice per TE)

Delay time: TR≦1.50 sec

Number of echoes: NE=100

All NMR data was collected on a removable disk. Data processing included the reformatting of the results-file and a phase correction procedure. The post-processing was done using Numar's standard software with multi-exponential fitting on the data of each result file. The software is named NNLS (EchoFit 3.2). The same procedure was followed whether the sample was bulk bitumen or ore.

Figure 17:
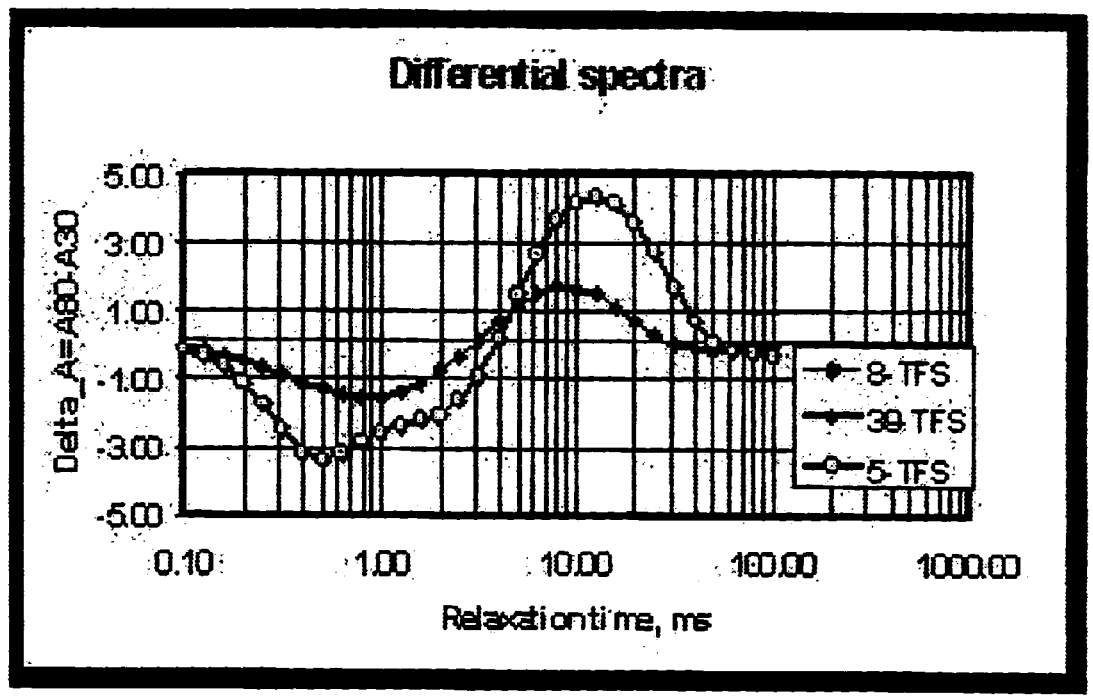
FIG. 17 shows the differential spectra of 3 different bitumen ore samples.
Figure 18:
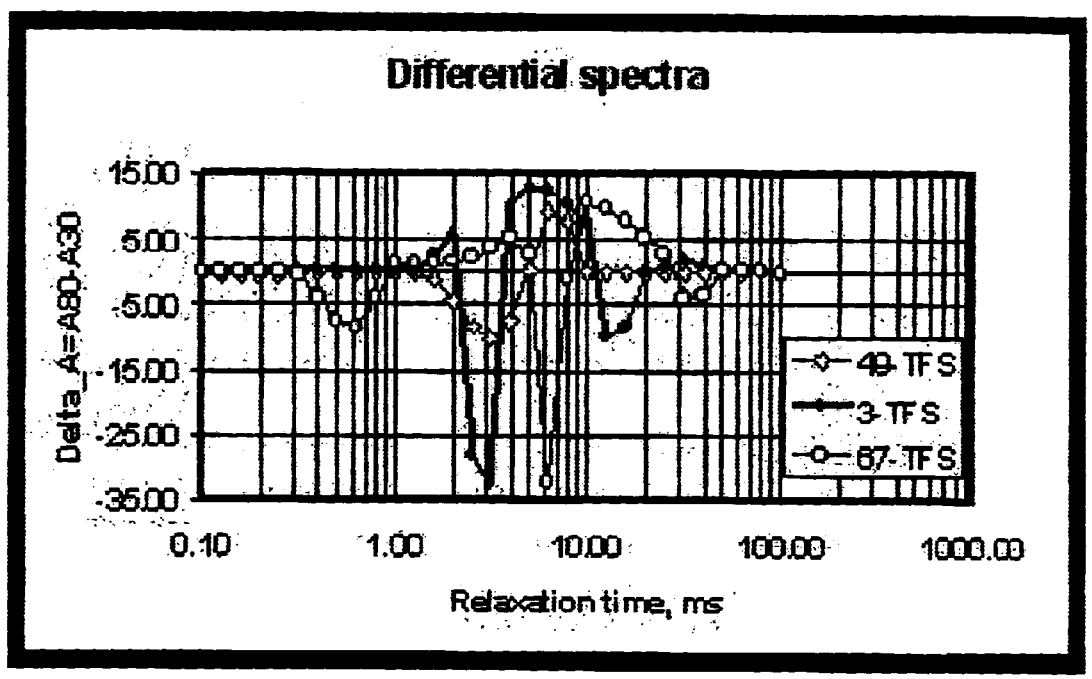
FIG. 18 shows the differential spectra of 3 different bitumen ore samples.

The spectra at 30° C. and at 80° C. of six representative samples from the same facies is shown in FIGS. 11 to 16. The samples are labelled 3-TFS, 5-TFS, 8-TFS, 39-TFS, 49-TFS and 67-TFS. The differential spectra of these samples are shown in FIGS. 17 and 18.

Oil and water content was determined for each of the samples by the methods described above and compared to the results obtained by Shell and by Core Laboratories by conventional Dean Stark analysis. The results are shown graphically in FIG. 19.

FIG. 19 is a comparison of all the oil fractions as determined by the methods of the present invention as compared to the same sample oil fractions determined by Dean Stark analysis in Shell Canada CRC. The scattering of the data results in a $R^2$ value of 0.83, which is acceptable. A significant part of the scattering is due to a few outliers. The possible interaction of clays is another possibility or distinctly different hydrogen index for the bitumen in these samples. Finally, metals present in the bitumen or in the solid matrix can affect the NMR spectra. Another possible reason for the discrepancy is the error associated with the mass balance in the extraction process. Based on data provided by Shell Canada, FIG. 20 shows the error bars associated with the extraction process. As a result of the data shown in FIG. 20, it may be seen that the NMR technology. In FIG. 21, the results of FIG. 19 are plotted on a set by set basis (as received by the inventors for testing). It can be observed that the first three sets had an excellent correlation ($R^2$=0.92–0.97) while the last set was poorer ($R^2$=0.81). All the outliers belonged to this latter set. When the same data is compared to another commercial laboratory's Dean Stark data, a similar correlation is obtained.

FIG. 22 shows the corresponding ore results for water content. The $R^2$ value is somewhat lower than the corresponding oil value, an observation that is consistent throughout this work. There seems to be an interference effect in the low $T_2$ terms of the NMR spectra. This effect can be attributed to same inaccuracy of water content determination due to the structural or mineralogical nature of bound water (in clays).

Example 2

14 oil sand samples (Samples A–N) were collected. The NMR spectra of each sample were determined at two different temperatures (30° C. and 80° C.) and the oil and water fractions determined in accordance with the method described above. Analysis was also undertaken using conventional Dean Stark analysis in two separate laboratories, to compare with and confirm the results of the present invention.

The results of the oil and water determination are presented in both tabular (Table 4) and graphical form (FIG. 23). Results for the weight percent of solids can be obtained by difference.

TABLE 4

NMR predictions of bitumen and water contents using two time echoes and average HI calculations

| Sample | Min Oil, % | Max Oil, % | Min Water, % | Max Water, % | Av. Oil | Av. Water |
|---|---|---|---|---|---|---|
| A | 6.03 | 6.92 | 10.90 | 11.22 | 6.48 | 11.06 |
| B | 14.08 | 16.19 | 6.11 | 7.08 | 15.13 | 6.59 |
| C | 4.63 | 5.34 | 5.58 | 6.11 | 4.98 | 5.84 |
| D | 8.95 | 10.29 | 12.40 | 12.93 | 9.62 | 12.66 |
| E | 6.58 | 7.55 | 9.22 | 10.01 | 7.06 | 9.62 |
| F | 13.39 | 15.41 | 3.21 | 3.98 | 14.40 | 3.59 |
| G | 13.75 | 14.07 | 5.04 | 5.25 | 13.91 | 5.15 |
| H | 16.57 | 17.8 | 4.13 | 4.42 | 17.19 | 4.28 |
| I | 7.76 | 8.72 | 10.15 | 10.32 | 8.24 | 10.24 |
| J | 7.97 | 15.01 | 6.35 | 7.76 | 11.49 | 7.06 |
| K | 7.57 | 9.07 | 6.22 | 6.27 | 8.32 | 6.25 |
| L | 13.72 | 15.51 | 5.15 | 5.51 | 14.62 | 5.33 |
| M | 14.03 | 16.57 | 2.52 | 3.43 | 15.30 | 2.98 |
| N | 11.14 | 13.23 | 1.17 | 1.59 | 12.19 | 1.38 |

Table 4 summarises the NMR predictions for oil and water using average HI for the bitumen and the water. In each sample, the weight percent values are plotted as minimum, maximum and average (arithmetic). In Table 5 and FIGS. 24 and 25, the results for the same samples are presented, but mow HI measured from each individual sample are used for the calculations. Also, the HI was adjusted for time echo.

TABLE 5

NMR predictions of bitumen and water contents using two time echoes and optimum HI calculations

| Sample | Min Oil, % | Max Oil, % | Min Water, % | Max Water, % | Av. Oil | Av. Water |
|---|---|---|---|---|---|---|
| A | 10.90 | 13.37 | 5.52 | 5.67 | 12.14 | 5.60 |
| B | 17.05 | 17.91 | 3.84 | 3.90 | 17.48 | 3.87 |
| C | 5.99 | 6.08 | 5.11 | 5.12 | 6.04 | 5.12 |
| D | 8.62 | 10.54 | 11.57 | 11.68 | 9.58 | 11.63 |
| E | 6.82 | 7.17 | 7.71 | 7.74 | 7.00 | 7.73 |
| F | 13.76 | 15.4 | 1.90 | 1.91 | 14.58 | 1.91 |
| G | 11.49 | 12.57 | 5.04 | 5.25 | 12.03 | 5.15 |
| H | 15.22 | 18.46 | 4.13 | 4.42 | 16.84 | 4.28 |
| I | 7.04 | 9.22 | 10.15 | 10.32 | 8.13 | 10.24 |
| J | 5.68 | 7.86 | 6.35 | 7.76 | 6.77 | 7.06 |
| K | 6.42 | 8.22 | 6.22 | 6.27 | 7.32 | 6.25 |
| L | 12.85 | 16.63 | 5.15 | 5.51 | 14.74 | 5.33 |
| M | 13.36 | 16.71 | 2.52 | 3.43 | 15.04 | 2.98 |
| N | 10.66 | 13.56 | 1.17 | 1.59 | 12.11 | 1.38 |

In FIG. 23, the results of average oil content using an average HI for the oil are compared to the results of the Dean Stark tests. If the agreement was exact all the points should fall in the same line (i.e. the diagonal). The results are close to the diagonal, with the exception of two outliers. The best fit of the data is with a line that has a $R^2=0.5925$. If the outliers are removed the correlation improves to $R^2=0.9452$. When the optimum HI values are used (FIG. 24), the correlation improves and it gives $R^2=0.9287$.

In FIG. 25, the corresponding results for water using optimum HI are shown. The correlation is very good ($R^2=0.879$). The results presented in FIGS. 24 and 25 indicate that use of the optimum HI provides an excellent correlation with conventional determinations.

In FIG. 26, the results of oil weight percent predictions for the two time-echo settings and different HI assumptions are compared for each sample. This figure offers an indication of the expected variability on the oil fraction predictions if the average calculation with optimum HI is dropped for another quicker measurement algorithm (i.e. single time-echo, average HI or both).

As will be apparent to those skilled in the art, various modifications, adaptations and variations of the foregoing specific disclosure can be made without departing from the scope of the present invention.

What is claimed is:

1. A method of determining the composition of a sample comprising bitumen or heavy oil and water in a porous media, said method comprising the steps of:
    (a) determining the NMR $T_2$ relaxation time spectrum of the same at a first low temperature;
    (b) heating the sample to a second elevated temperature;
    (c) determining the NMR $T_2$ relaxation time spectrum of the sample at the elevated temperature;
    (d) creating a differential spectrum by subtracting a signal amplitude ($A^{Low}$) of the low temperature spectrum from a signal amplitude ($A^{High}$) of the elevated temperature spectrum to determine a differential amplitude ($\Delta A$);
    (e) determining the water content by summing the amplitudes of the low temperature spectrum for the $T_2$ range where 2.5 ms $<T2<3000$ ms and dividing by the amplitude index (AI) of water; and
    (f) determining the heavy oil or bitumen content by summing
        (i) the amplitudes of the elevated temperature spectrum in the T2 range where, in the differential spectrum, $\Delta A$ has a negative value; and
        (ii) the amplitudes of the differential spectrum where $\Delta A$ has a positive value; and
        (iii) dividing byte amplitude index (AI) of heavy oil or bitumen at the elevated temperature."

2. The method of claim 1 wherein the low temperature is between about 20° C. to about 40° C.

3. The method of claim 1 wherein the elevated temperature is between about 70° C. to about 90° C.

4. The method of claim 1, 2 or 3 wherein the low temperature is about 30° C. and the elevated temperature is about 80° C.

5. The method of claim 1 wherein the AI of heavy oil or bitumen at the elevated temperature is measured determined by measuring the AI of sample of the heavy oil or bitumen, isolated from the mixture sample.

6. A system for determining the composition of a sample comprising bitumen or heavy oil and water in a porous media, said system comprising:
    (a) means for determining the NMR $T_2$ relaxation time spectrum of the sample at a first low temperature;
    (b) meant for determining the NMR $T_2$ relaxation time spectrum of the sample at a second elevated temperature;
    (c) means for creating a differential spectrum by subtracting a signal amplitude ($A^{Low}$) of the low temperature spectrum from a signal amplitude ($A^{High}$) of the elevated spectrum to determine a differential amplitude ($\Delta A$);
    (d) means for determining the water content by summing the amplitudes of the low temperature spectrum for the $T_2$ range where 2.5 ms $<T2<3000$ ms and dividing by the amplitude index (AI) of water; and
    (e) means for determining the heavy oil or bitumen content by summing
        (i) the amplitudes of the elevated temperature spectrum in the T2 range where, in the differential spectrum, $\Delta A$ has a negative value; and
        (ii) the amplitudes of the differential spectrum where $\Delta A$ has a positive value; and
        (iii) dividing by the AI amplitude index (AI) of heavy oil or bitumen at the elevated temperature."

* * * * *